United States Patent
Liu et al.

(10) Patent No.: US 11,697,807 B2
(45) Date of Patent: Jul. 11, 2023

(54) ELECTROCHEMICAL BIOSENSOR

(71) Applicant: CASE WESTERN RESERVE UNIVERSITY, Cleveland, OH (US)

(72) Inventors: Chung Chiun Liu, Cleveland Heights, OH (US); Yifan Dai, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 379 days.

(21) Appl. No.: 17/039,360

(22) Filed: Sep. 30, 2020

(65) Prior Publication Data
US 2021/0246436 A1    Aug. 12, 2021

Related U.S. Application Data

(60) Provisional application No. 62/908,266, filed on Sep. 30, 2019.

(51) Int. Cl.
*C12N 9/22*      (2006.01)
*C12N 15/113*    (2010.01)
(Continued)

(52) U.S. Cl.
CPC .............. *C12N 9/22* (2013.01); *C12N 15/113* (2013.01); *C12Q 1/68* (2013.01); *G01N 27/3275* (2013.01)

(58) Field of Classification Search
None
See application file for complete search history.

(56) References Cited

U.S. PATENT DOCUMENTS

RE40,198 E      4/2008  Buck, Jr. et al.
7,935,191 B2    5/2011  Mutharasan et al.
(Continued)

FOREIGN PATENT DOCUMENTS

EP       2492351 A2    8/2012
WO    2002/047680 A2    6/2002
(Continued)

OTHER PUBLICATIONS

J.S. Chen, et al. ("CRISPR-Cas12a target binding unleashed indiscriminate single-stranded DNase activity", Science, 360(6387): p. 436-439 & Supplemental p. S1-S28, Apr. 2018.*
(Continued)

*Primary Examiner* — J. Christopher Ball
(74) *Attorney, Agent, or Firm* — Tarolli, Sundheim, Covell & Tummino, L.L.P.

(57) ABSTRACT

A CRISPR electrochemical biosensing system (E-CRISPR) for detection of analytes includes a disposable, microfabricated three-electrode sensor that includes a working electrode, a counter electrode, a reference electrode, and a nonspecific ssDNA reporter with an electrochemical tag for signal transduction tethered to a surface of the working electrode; and a Cas12a-crRNA duplex that is designed to specifically recognize and cleave target nucleic acid strand based on the protospacer adjacent motif (PAM) sequence of the target and crRNA sequence, wherein the PAM recognition depends on specific 5' TTTN nucleic acid sequence located at an opposite strand of a recognition strand, and wherein only upon the recognition of the PAM sequence by the Cas protein, the Cas protein, acting as a DNA helicase, unwinds the target DNA.

2 Claims, 16 Drawing Sheets

(51) Int. Cl.
  *G01N 27/327* (2006.01)
  *C12Q 1/68* (2018.01)

(56) References Cited

U.S. PATENT DOCUMENTS

| | | |
|---|---|---|
| 8,834,702 B2 | 9/2014 | Lin et al. |
| 2004/0106190 A1 | 6/2004 | Yang et al. |
| 2005/0136500 A1 | 6/2005 | Yang et al. |
| 2006/0272958 A1 | 12/2006 | Lee |
| 2008/0027135 A1 | 1/2008 | Sondek et al. |
| 2009/0017197 A1 | 1/2009 | Zhang et al. |
| 2010/0209415 A1 | 8/2010 | Smith et al. |
| 2010/0292178 A1 | 11/2010 | Young |
| 2011/0076739 A1 | 3/2011 | Mccauley et al. |
| 2011/0155576 A1 | 6/2011 | Hwang et al. |
| 2011/0200606 A1 | 8/2011 | Mccauley et al. |
| 2011/0210017 A1 | 9/2011 | Lai et al. |
| 2012/0046181 A1 | 2/2012 | Harb et al. |
| 2013/0020065 A1 | 1/2013 | Tubel et al. |
| 2013/0065257 A1 | 3/2013 | Wang et al. |
| 2014/0005068 A1 | 1/2014 | Das et al. |
| 2014/0011691 A1 | 1/2014 | Sierks et al. |
| 2014/0174950 A1 | 6/2014 | Gooding et al. |

FOREIGN PATENT DOCUMENTS

| | | |
|---|---|---|
| WO | 2003/040694 | 5/2003 |
| WO | 2004/021000 A1 | 3/2004 |
| WO | 2004/061418 A2 | 7/2004 |
| WO | 2009/035791 A1 | 3/2009 |
| WO | 2010/104595 A1 | 9/2010 |
| WO | 2011/022670 A1 | 2/2011 |
| WO | 2014/032044 A1 | 2/2014 |

OTHER PUBLICATIONS

First Named Inventor: Chung Chiun Liu; Title: System and Methods for the Detection of Biomarkers of Neurodegenerative Disorders; U.S. Appl. No. 15/970,738, filed May 3, 2018; Final Office Action; dated Sep. 22, 2020.

First Named Inventor: Chung Chiun Liu; Title: System and Methods for the Detection of HBA1C; U.S. Appl. No. 15/973,218, filed May 7, 2018; Final Office Action; dated Sep. 1, 2020.

First Named Inventor: Chung Chiun Liu; U.S. Appl. No. 16/499,757, filed Sep. 30, 2019 Non-Final Office Action; dated Nov. 10, 2022; 28 pgs.

First Named Inventor: Chung Chiun Liu; Title: System and Method for Detecting Lysyl Oxidase-Like 2 Protein (LOXL2) and Breast Cancer; U.S. Appl. No. 16/168,630, filed Oct. 23, 2018; Office Action; dated Sep. 21, 2020, 7 pgs.

First Named Inventor: Chung Chiun Liu; Title: System and Methods for the Detection of Biomarkers of Glypican-1; U.S. Appl. No. 16/118,216, filed Aug. 30, 2018; Final Office Action; dated Oct. 8, 2020.

Karalemas et al., Taianta, 2000, 53:391-402.

Moreno-Bueno, et al., EMBO Mol Med., 2011, 3:528-544.

Puneet et al., "Identification of S-nitroso-CoA reductases that regulate protein S-nitrosylation", Proceedings of the National Academy of Sciences, vol. 111, No. 52, Dec. 15, 2014 (Dec. 15, 2014).

Puneet et al., "Purification and Characterization of Novel Denitrosylases from Yeast and Mammals", Dec. 31, 2012 (Dec. 31, 2012), Abstract.

Q. Xue, et al. "An integrated micro immunosensor for hemoglobin-A1c level detection", In Pr5oceedings of 2010 IEEE/ASME International Conference on Mechatronic and Embedded Systems and Applications, p. 208-212, Jul. 2010.

Zhang, S., et al., An ultrasensitive electrochemical immunosensor for determination of estradiol using coralloid Cu2S nanostructures as labels, RSC Adv., 2015, 5, pp. 6512-6517.

Chen, Kuan-Jung, et al., "Bimetallic PtM (M=Pd, Ir) nanoparticle decorated multi-walled carbon nanotube enzymeree, mediator-less amperometric snesorfor H2O2", Biosensors and Bioelectronics, vol. 33, No. 1, Mar. 1, 2012.

Chinese Office Action dated Sep. 2, 2016.

Chinese Office action for Patent Application No. 201580028310.7, dated Jun. 28, 2018.

Dixon, Biochemical Education, 1975, 3(2):31-33.

European Office action for Patent Application No. 15799206.6-1118, dated May 8, 2018.

European Search Report for Application No. 15799206.6-1408 I 3149466 PCT/US2015032609, dated Oct. 20, 2017.

First Named Inventor: Chung Chiun Liu; U.S. Appl. No. 17/039,360, filed Sep. 30, 2020; Non-Final Office Action; dated Dec. 14, 2022; 7 pgs.

He Yahui, et al., "A New Optimized Spectrophotometric Assay for the Measurement of Pyruvate Dehydrogenase's Activity", Laboratory of Environmental Science, 2007, pp. 418-421.

Herranz, et al., "Lysyl oxidase-like 2 deaminates lysine 4 in histone H3", Molecular Cell. vol. 46, Issue 3, pp. 36-376, May 11, 2012.

Hinman et al. JBC, 1981, 256:6583-6586.

Howell et al. Clin Chem., 1979, 25(2):269-272.

Janyasupab et al. J of Nanotechnology, 2011, pp. 1-6.

Janyasupab, Metini, "New Designs of Electrochemical H2O2 Based Biosensors for Advanced Medical Diagnosis", PhD Thesis, May 1, 2013, pp. 1-114.

Kim et al., "Impedometric estrogen biosensor based on estrogen receptor alpha-immobilized gold electrode", Journal of Electroanalytical Chemistry, 671 (2012), pp. 106-111.

Kirschmann, et al. "A Molecular Role for Lysyl Oxidase in Breast Cancer Invasion", Cancer Research, 62(15), 2002, pp. 4478-4483.

Lin, Po-Yuan, et aL, "Detection of Alpha-Methylacyl-CoA Racemase (AMACR), a Biomarker of prostate Cancer, in Patient Blood Samples Using Nanoparticle Electrochemical Biosensor", Biosensor MDPAAG, Ch, vol. 2, No. 4, Sep. 26, 2012.

Office Action for Chinese Application No. 201380051094.9, dated Jan. 23, 2017.

Office action for European Patent Application No. 13 840 525.3-1408, dated Nov. 6, 2017.

Pushpa et al., "Role of pyruvate dehydrogenase complex in traumatic brain injury and Measurement of pyruvate dehydrogenase enzyme by dipstick test", Journal of Emergencies, Trauma, and Shock May 2009, vol. 2, No. 2, May 2009 (May 2009), pp. 67-72.

Shen, et al., "An iridium nanoparticles dispersed carbon based thick film electrochemical biosensor and its application or a single use, disposable glucose biosensor", Sensors and Actuators B, vol. 125 (2007) pp. 106-113.

Supplementary European Search Report for Application No. EP 15 79 9021, dated Sep. 14, 2017.

Warriner et al., "A lactate dehydrogenase amperometric pyruvate electrode exploiting direct detection of NAD+ at a poly (3-methylthiopene) :poly (phenol red) modified plöatinum surface", Jan. 1, 1997 (Jan. 1, 1997), pp. 91-99.

\* cited by examiner

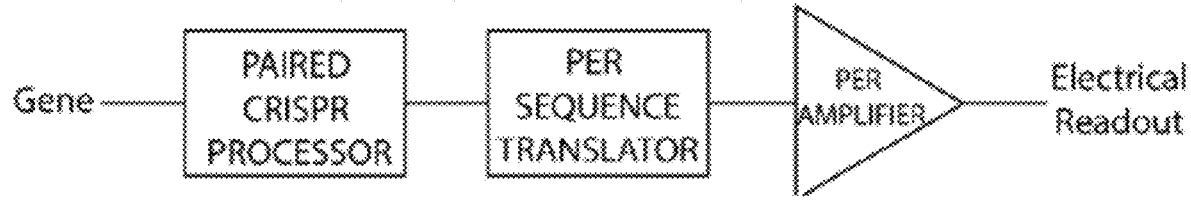
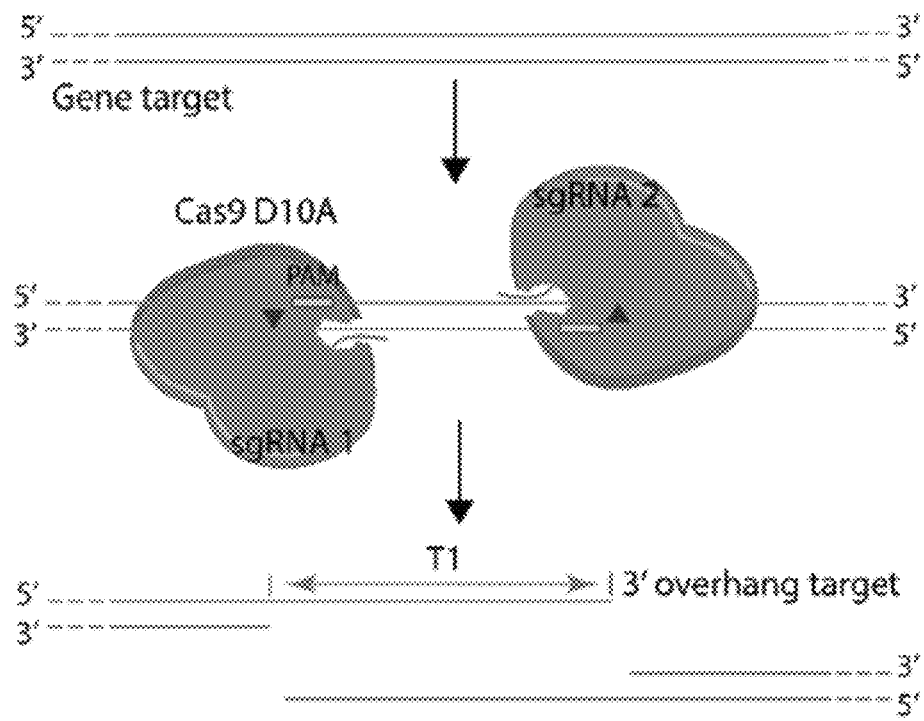
Fig. 5A
Fig. 5B c. Primer Exchange Reaction Mediated Translator and Amplifier d. Autonomous Construction of Signaling Electrochemical Interface

ELECTROCHEMICAL BIOSENSOR

RELATED APPLICATION

This application claims priority from U.S. Provisional Application No. 62/908,266, filed Sep. 30, 2019, the subject matter of which is incorporated herein by reference in its entirety.

BACKGROUND

An accurate, rapid, and cost-effective sensing strategy for the quantification of disease biomarkers is vital for the development of early-diagnostic point-of-care systems, further leading to personalized medicine and benefiting overall human health. Electrochemistry based biosensing platforms have been widely developed, owing to its rapid signal readout, affordable transduction element and simple sensing platform. One of the critical challenges for such sensing system is its accuracy. Recent robust developments of CRISPR (clustered regularly interspaced short palindromic repeats) based gene editing systems demonstrated the accuracy of the CRISPR system in targeting nucleic acids owing to the complementarity dependent CRISPR cleavage event. Utilizing the Cas-crRNA target recognition-and-cleavage event induced collateral (trans) cleavage effect of the non-specific ssDNA reporter, CRISPR type III, V, VI RNA guided nucleases (Csm6, Cas12a, Cas13) have been applied for the detection of nucleic acid (RNA/DNA) through fluorescence transduction system.

SUMMARY

Embodiments described herein relate to a CRISPR electrochemical biosensing system (E-CRISPR) that can detect different categories of analytes for clinical applications. Advantageously, the E-CRISPR is cost-efficient, portable, and provides robust point-of-care system. The E-CRISPR based sensing system can detect, for example, small molecules including biomolecules, such as nucleic acids, peptides, and proteins, in a sample of interest.

The E-CRISPR includes a simple transduction method for CRISPR type III, V, VI nucleases based sensing systems and provides a new liberty in the classes of analytes the sensing system can detect. The E-CRISPR includes disposable, micro-fabricated three-electrode sensor that can include, for example, a gold working electrode and counter electrode and Ag/AgCl as the reference electrode. The E-CRISPR can also include Cas12a-crRNA duplex that is designed to specifically recognize and cleave target nucleic acid strand based on the protospacer adjacent motif (PAM) sequence of the target and crRNA sequence (FIG. 1A). The PAM recognition depends on the specific 5' TTTN nucleic acid sequence located at an opposite strand of a recognition strand. Only upon the recognition of the PAM sequence by the Cas protein, the Cas protein, acting as a DNA helicase, would unwind the target DNA. After the separation of the target strands, the complementarity (between crRNA and target) dependent cleavage activity can further be activated. To achieve the electrochemical transduction of CRISPR detection signal, the target cis-cleavage initiated trans-cleavage (collateral cutting) effect of Cas12a on the nonspecific ssDNA is probed through an electrochemical method using the electrochemical sensor. A nonspecific ssDNA reporter is designed with an electrochemical tag, such as methylene blue (MB), for signal transduction and a thiol moiety to tether on the sensor surface in order to acquire the signal electrically (FIG. 1B). Consequently, the electron transfer process between the gold electrode and the redox active species on the ssDNA can be electrochemically initiated and transduced. With the presence of the target, the Cas12a trans-cleavage activity is activated, cleaving the MB-ssDNA reporter off the electrode surface, therefore decreasing the MB signal transduced (FIG. 1C). Without the presence of the target, the Cas12a trans-cleavage activity is silenced, retaining the MB-ssDNA reporter on the surface (FIG. 1D). A representation of electrochemical signal output based on the conditions without/with target is shown in FIG. 1E. The design of the MB-ssDNA reporter covered electrode is generally applicable for any CRISPR type III, V and VI systems as a simple and cost-effective signal transduction strategy.

For protein and small molecule detection, aptamer can be widely applied as a recognition element due to its high-selectivity, low cost, and high-binding affinity. Specific aptamer targeting protein or small molecule to treat the sample of interest. Cas12a-crRNA is specifically designed to the recognize the aptamer. E-CRISPR can evaluate the concentration of aptamer left after sample treatment. The concentration of aptamer is reversely correlated with the amount of protein or small molecule of interest. In the presence of a target or target condition, a small amount of aptamer can be detected. Therefore, the trans-cleavage activity is mutated indicating a high methylene blue signal. In the absence of a target or target condition, a high amount of aptamer can be detected with a highly activated trans-cleavage, indicating a low methylene blue signal.

In some embodiments, the E-CRISP can include an autonomous and programmable multi-functional heterogeneous biochemical circuit that can identify, transform, translate, and amplify detected biological or small molecule signals into physicochemical signals based on logic design principles. The E-CRISPR can include a. CRISPR-array-mediated primer-exchange-reaction-based biochemical circuit cascade, which probes a specific biomolecular input, transforms the input into a structurally accessible form for circuit wiring, translates the input information into an arbitrary sequence, and finally amplifies the prescribed sequence through autonomous formation of a signaling concatemer. This upstream biochemical circuit can be further wired with a downstream electrochemical interface, delivering an integrated bioanalytical platform.

It will be appreciated the operation of the E-CRISPR involves various parameters. Therefore, any variations of these parameters are also encompassed by the present disclosure. These variations include different types of Cas protein orthologs (e.g., in the Cas III and V system), magnesium ion ($Mg^{2+}$) concentration, manganese ion ($Mn^{2+}$) concentration, reaction temperature and time, surface ssDNA reporter sequence, surface ssDNA reporter length, and sensor prototypes.

DETAILED DESCRIPTION

Embodiments described herein relate to a CRISPR electrochemical biosensing system (E-CRISPR) that can detect different categories of analytes for clinical applications. Advantageously, the E-CRISPR is cost-efficient, portable, and provides robust point-of-care system. The E-CRISPR based sensing system can detect, for example, small molecules including biomolecules, such as nucleic acids, peptides, and proteins, in a sample of interest.

Figures 1A, 1B, 1C, 1D, 1E:
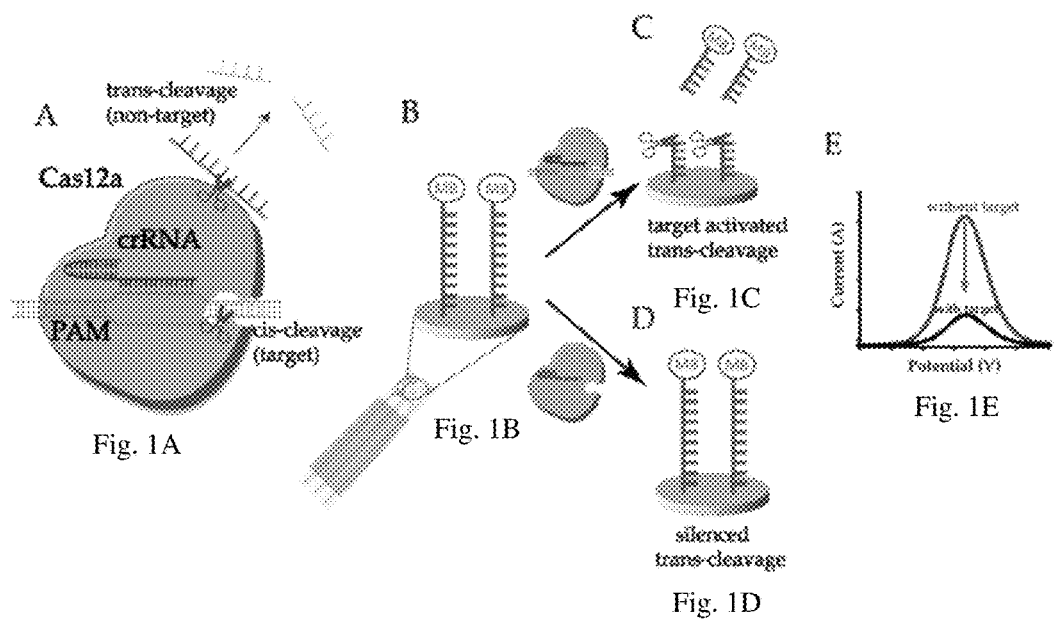
FIGS. 1(A-E) illustrate the principle of E-CRISPR. A) Cas12a (cpf1) performs crRNA guided cis-cleavage (specific target) initiated trans-cleavage activity (nonspecific ssDNA). B) Nonspecific ssDNA reporter with methylene blue tag immobilized on the gold electrode. C) With the presence of the target, Cas12a-crRNA would initiate the trans-cleavage activity on nonspecific ssDNA reporter, resulting a low electrochemical current of methylene blue. D) Without the presence of the target, Cas12a-crRNA would not initiate the trans-cleavage activity on nonspecific ssDNA reporter, resulting a high electrochemical current of methylene blue. E) A representation of electrochemical current outputs based on the without & with target conditions.

The E-CRISPR includes a simple transduction method for CRISPR type III, V, VI nucleases based sensing systems and provides a new liberty in the classes of analytes the sensing system can detect. The E-CRISPR includes disposable, micro-fabricated three-electrode sensor that can include, for example, a gold working electrode and counter electrode and Ag/AgCl as the reference electrode. The E-CRISPR can also include Cas12a-crRNA duplex that is designed to specifically recognize and cleave target nucleic acid strand based on the protospacer adjacent motif (PAM) sequence of the target and crRNA sequence (FIG. 1A). The PAM recognition depends on the specific 5' TTTN nucleic acid sequence located at an opposite strand of a recognition strand. Only upon the recognition of the PAM sequence by the Cas protein, the Cas protein, acting as a DNA helicase, would unwind the target DNA. After the separation of the target strands, the complementarity (between crRNA and target) dependent cleavage activity can further be activated. To achieve the electrochemical transduction of CRISPR detection signal, the target cis-cleavage initiated trans-cleavage (collateral cutting) effect of Cas12a on the nonspecific ssDNA is probed through an electrochemical method using the electrochemical sensor. A nonspecific ssDNA reporter is designed with an electrochemical tag, such as methylene blue (MB), for signal transduction and a thiol moiety to tether on the sensor surface in order to acquire the signal electrically (FIG. 1B). Consequently, the electron transfer process between the gold electrode and the redox active species on the ssDNA can be electrochemically initiated and transduced. With the presence of the target, the Cas12a trans-cleavage activity is activated, cleaving the MB-ssDNA reporter off the electrode surface, therefore decreasing the MB signal transduced (FIG. 1C). Without the presence of the target, the Cas12a trans-cleavage activity is silenced, retaining the MB-ssDNA reporter on the surface (FIG. 1D). A representation of electrochemical signal output based on the conditions without/with target is shown in FIG. 1E. The design of the MB-ssDNA reporter covered electrode is generally applicable for any CRISPR type III, V and VI systems as a simple and cost-effective signal transduction strategy.

For protein and small molecule detection, aptamer can be widely applied as a recognition element due to its high-selectivity, low cost, and high-binding affinity. Specific aptamer targeting protein or small molecule to treat the sample of interest. Cas12a-crRNA is specifically designed to the recognize the aptamer. E-CRISPR can evaluate the concentration of aptamer left after sample treatment. The concentration of aptamer is reversely correlated with the amount of protein or small molecule of interest. In the presence of a target or target condition, a small amount of aptamer can be detected. Therefore, the trans-cleavage activity is mutated indicating a high methylene blue signal. In the absence of a target or target condition, a high amount of aptamer can be detected with a highly activated trans-cleavage, indicating a low methylene blue signal.

In some embodiments, the E-CRISP can include an autonomous and programmable multi-functional heterogeneous biochemical circuit that can identify, transform, translate, and amplify detected biological or small molecule signals into physicochemical signals based on logic design principles. The E-CRISPR can include a CRISPR-array-mediated primer-exchange-reaction-based biochemical circuit cascade, which probes a specific biomolecular input, transforms the input into a structurally accessible form for circuit wiring, translates the input information into an arbitrary sequence, and finally amplifies the prescribed sequence through autonomous formation of a signaling concatemer. This upstream biochemical circuit can be further wired with a downstream electrochemical interface, delivering an integrated bioanalytical platform.

It will be appreciated the operation of the E-CRISPR involves various parameters. Therefore, any variations of these parameters are also encompassed by the present disclosure. These variations include different types of Cas protein orthologs (e.g., in the Cas III and V system), magnesium ion ($Mg^{2+}$) concentration, manganese ion ($Mn^{2+}$) concentration, reaction temperature and time, surface ssDNA reporter sequence, surface ssDNA reporter length, and sensor prototypes.

Example 1

This example describes a system or platform that can be used as a universal biosensing strategy for the detection and quantification of nucleic acids, peptides, proteins and small molecules. Owing to the high-specificity of target recognition, other than gene editing tool, we utilized the CRISPR Type V system, Cas12a (cpf1) as an efficient biosensing system, which translates the target recognition activity electrode constructed with non-specific ssDNA. Various factors were investigated to produce an optimized on-chip trans-cleavage activity for a high-sensitivity E-CRISPR detection platform. Moreover, our preliminary implementation illustrates that the E-CRISPR system can be applied not only for nucleic acid sensing; with the addition of an aptamer based sensing cascade, the E-CRISPR can also be utilized for protein detection, providing a generalizable, robust and cost-effective detection system.

Materials and Methods

Fabrication of ssDNA Reporter Surface

An array containing twenty sensors was first cleaned through an established procedure using potassium hydroxide, sulfuric acid and nitric acid. Thiol linked ssDNA reporter was treated with 10 μM of tris(2-carboxyethyl) phosphine (TCEP) to reduce the S-S bond for 10 min in the dark at room temperature. The ssDNA reporter was then diluted to 1 μM using 10 mM Tris buffer containing 10 mM EDTA. 20 μL of the 1 μM ssDNA reporter was directly incubated onto the gold sensor for 1 hr in the dark at room temperature. The ssDNA immobilized sensor array was then cleaned by immersing in 10 mM Tris buffer for 5 min. After cleaning, the sensor array was immersed in 2 mM 6-mercaptoheaxnol (MCH) prepared in 10 mM Tris buffer for 30 min to passivate the surface and replace loosely tethered ssDNA reporter, forming a highly-aligned surface (Operation of MCH related steps should be conducted in a fume hood due to its toxicity). After the MCH treatment, the sensor array was then cleaned by immersing in 10 mM Tris buffer for 5 min. The cleaned sensor array was then dried by nitrogen gas and ready for treatment by CRISPR system. For a short storage period, the cleaned sensor array can be stored in 10 mM Tris buffer (containing 100 mM NaCl) at 4° C.

In Vitro Digestion of Cas12a-crRNA

Cas12a-crRNA duplex was prepared in a buffer prepared by nuclease free water containing 50 mM NaCl, 10 mM Tris-HCl, 15 mM MgCl2, 100 µg/ml BSA with a pH of 7.9. 30 nM of Cas12a-crRNA was assembled and incubated at 25° C. for 10 min. Typically, for nucleic acid detection, 4 µL of sample was added into 26 µL of the Cas12a-crRNA duplex to form the Cas12a-crRNA-target triplex and incubated for 10 min at room temperature. 20 µL of the Cas12a-crRNA-target triplex solution was applied to ssDNA reporter covered sensor for trans-cleavage activity at 37° C. for 30 min. 80 U/mL of Proteinase k was applied to the CRISPR treated surface at 37° C. for 15 min before the electrochemical analysis. For protein detection, 10 µL of 100 nM of aptamer was applied to treat 10 µL of sample (resulting in a 50 nM final concentration of aptamer) and incubated at room temperature for 30 min. E-CRISPR as described above was then applied for protein sample analysis with an elongated trans-cleavage period for 60 min.

On-Chip Electrochemical Analysis

After the on-chip CRISPR reaction, the sensors were cleaned by immersing the sensors into a 10 mM Tris buffer for 5 min. For electrochemical test, a 10 mM Tris buffer containing 100 mM NaCl was applied as the electrolyte. Square wave voltammetry (SWV) was applied before and after the treatment of Cas12a-crRNA-target triplex to obtain the change of current based on a potential range of −0.6V to −0.1V, a frequency of 25 Hz, an amplitude of 25 mV (variation of frequency (15 Hz-120 Hz) and amplitude (25 mV-50 mV) did not present significant enhancement of the quantity of signal changed or the signal stability).

Clinical Sample-Mesenchymal Stem Cell (MSCs) Culture and Differentiation

Cultures of human bone marrow-derived MSCs from healthy de-identified adult volunteer donors were established as previously described. The bone marrow was collected using a procedure reviewed and approved by the University Hospitals of Cleveland Institutional Review Board; informed consent was obtained from all de-identified donors. Cells were expanded in DMEM-LG supplemented with 10% fetal bovine serum, supplemented with FGF2 (10 ng/ml of) for 14 days. Cells were trypsinized and then resuspended in chondrogenic differentiation medium consisting of DMEM-high glucose supplemented with 1% ITS+, $10^{-7}$ M dexamethasone, 1 mM sodium pyruvate, 120 mM ascorbic acid-2 phosphate, 100 mM nonessential amino acids, and 10 ng/mL TGF-β1 protein. Two hundred microliters of this cell suspension containing 250,000 cells was added per well of a 96-well polypropylene V-bottom, multi-well dish (Phenix Research). The multi-well plates were centrifuged at 500 g for 5 min and then incubated at 37° C. The differentiation medium was changed every other day. Conditioned medium from these pellets was collected at different time points. Days 2 and 28 were chosen to use in the biosensor platform based on previous transcriptome data (RNAseq) showing a greater difference in TGF-β1 protein expression between days 2 and 28. To activate the latent secreted TGF-β1 protein to the detectable form, 20 µL of 1 M HCl were added to 100 µL of conditioned medium and incubated for 10 minutes and then neutralized with 20 µL of 1.2 M NaOH/0.5 M HEPES. The samples were assayed immediately. This procedure ensures that only the secreted version of TGF-β1 protein assayed.

Results

Verification of E-CRISPR on Nucleic Acid Detection

Figures 2A, 2B, 2C:
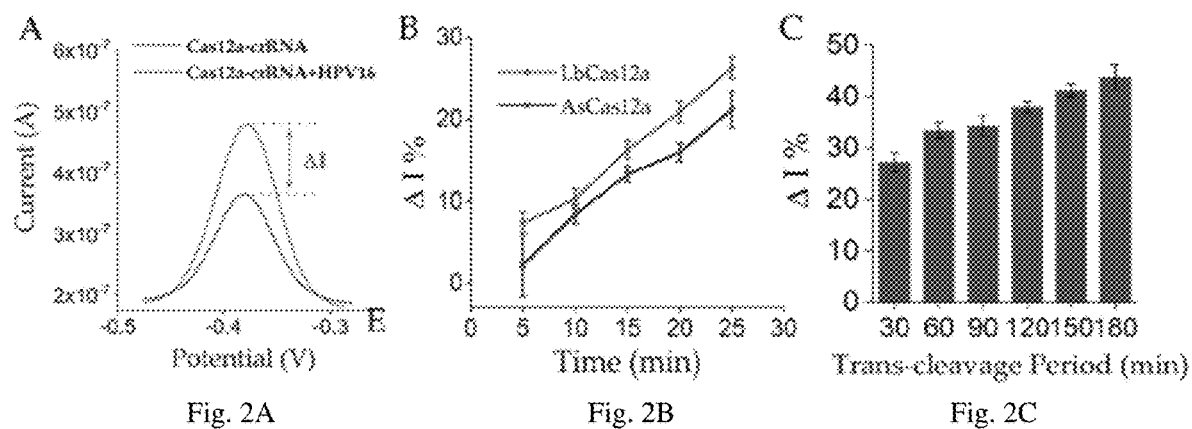
FIGS. 2(A-H) illustrates optimization of on-chip trans-cleavage activity.
A) Representation of square wave voltammetry (SWV) evaluation of E-CRISPR in response to HPV-16. Red curve represents the background signal of 50 nM of Cas12a-crRNA duplex. Black curve represents the signal generated by the 50 nM of Cas12a-crRNA-target induced trans-cleavage activity. B) Evaluation of 50 nM of Cas12a orthologs from Lachnospiraceae bacterium and Acidaminococcus sp on its activity for on-chip trans-cleavage activity based on the change of current between background signal and target-mediated signal. ΔI %=Background signal–Target signal. (Red line—LbCas12a; Black line—AsCas12a).
C) Evaluation of trans-cleavage activity using 50 nM of LbCas12a-crRNA-target triplex. D) Background signal Evaluation of the effect of the concentration of divalent metal ions on the trans-cleavage activity of RuvC domain based on 50 nM of LbCas12a-crRNA-target triplex. E) & F) & G) SWV graphs of different lengths of surface ssDNA reporters based on 30 nM of LbCas12a-crRNA-target triplex. H) Comparison of signal change from different lengths of surface ssDNA reporters. SWV graphs in these figures present the result of a single test. Error bars in figures present the standard error (SE) based on at least three individual trails using at least three different sensors.

To examine the feasibility of the E-CRISPR on nucleic acid detection, a human papilloma virus (HPV) subtype, HPV-16, which is critical to carcinogenesis, was selected as the target. A target sequence in the L1-encoding gene of HPV16 was identified based on the TTTN PAM sequence required by the Cas12a endonuclease. The electrochemical biosensing platform was initially developed based on the Cas12a endonuclease from Acidaminococcus sp (AsCas12a). We first investigated the on-chip collateral cleavage performance based on the AsCas12a-crRNA duplex targeting the HPV-16 sequence. After assembling the HPV-16 and the AsCas12a-crRNA, the triplex complex was directly incubated onto the ssDNA reporter covered electrode. Square wave voltammetry (SWV) was applied to evaluate the MB signal, which was decreased only in the presence of the cognate target with corresponding AsCas12a-crRNA (FIG. 2A).

Evaluation of the Optimized Condition for On-Chip Trans-Cleavage Activity

For biosensing application, the detection sensitivity is critical due to the low abundance of clinically relevant biomarkers in human fluids. For the E-CRISPR detection platform, the trans-cleavage activity is the key for signal transduction, and therefore is critical to the sensitivity performance. We first compared the on-chip trans-cleavage activity of another type of Cas12a protein, Lachnospiraceae bacterium ND2006 Cas12a (LbCas12a), with that of the AsCas12a. LbCas12a demonstrated a more apparent and stable trans-cleavage response within 5 min comparing with that of AsCas12a (FIG. 2B). F, LbCas12a presented a more robust trans-cleavage activity within the testing period based on the same experimental condition, therefore LbCas12a was selected for further E-CRISPR development. We further evaluated the possible factors that may affect the trans-cleavage activity for on-chip electrochemical test using HPV-16 as the target. The optimized trans-cleavage period was investigated. The ΔI % continuously increased with the increasing incubation time for the collateral cleavage event (FIG. 2C). It is interesting to notice that the trans-cleavage activity is not a simultaneous event of the cis-cleavage activity after the activation of cis-cleavage by the target. Because, the cis-cleavage of target strand is typically finished within 30 min; however, the trans-cleavage function remained active even after 3 hours (FIG. 2C), indicating the target recognition and cis-cleavage activity of Cas12a system is the activator for the trans-cleavage domain of the Cas12a endonuclease.

Figure 2D:
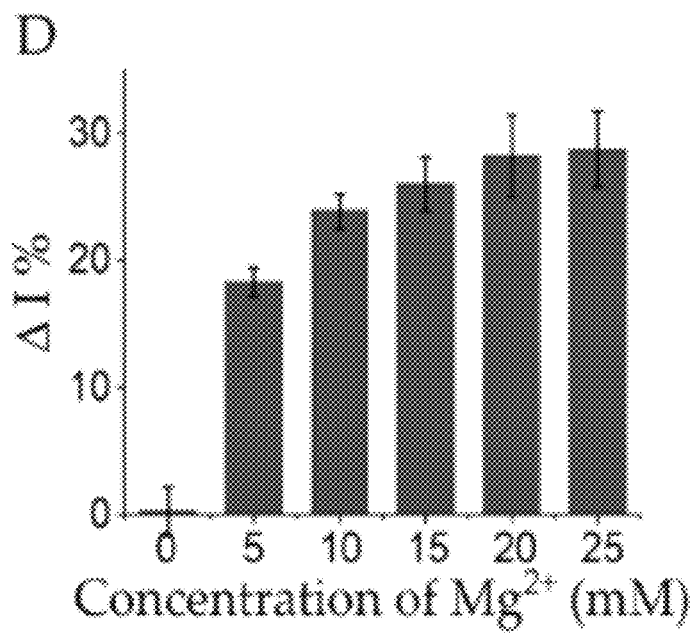

We further investigated the chemical environment of the Cas12a to optimize the trans-cleavage performance. An important factor that may affect the Cas12a cleavage activity is the divalent cation $Mg^{2+}$ concentration in the testing solution. Cas12a RuvC domain is known to cleave ssDNA through the two-metal ion mechanism, which involves the $Mg^{2+}$ ions to induce conformational coordination of the RuvC domain and the ssDNA by shifting the spatial distribution of ssDNA around the RuvC active cutting center. Therefore, we evaluated the effect of concentration of $Mg^{2+}$ ions in the in vitro cleavage solution on the performance of trans-cleavage activity. The trans-cleavage activity was only activated with the presence of the $Mg^{2+}$ ions in the testing solution (FIG. 2D). Increasing concentration of $Mg^{2+}$ cations up to 15 mM demonstrated an enhanced trans-cleavage activity. Hence, an optimized $Mg^{2+}$ concentration of 15 mM was selected for the preparation of Cas12a-crRNA duplex.

In order to perform an efficient surface chemistry based trans-cleavage, the accessibility of Cas12a endonuclease to the nonspecific ssDNA is important. Thus, we evaluated the effect of ssDNA reporter density on the electrode surface on the variation of electrochemical signal before and after trans-cleavage activity. An ideal surface condition can provide an optimized electrostatic environment for charged phosphate backbones and the hydroxyl groups of the passivation agents to ensure an upright ssDNA surface, facilitating the cleavage activity. The surface density of ssDNA reporter was manipulated by the concentration of the ssDNA reporter incubation solution. A high surface density of ssDNA reporter significantly decreased the change of signal, because this high surface density decreased the accessibility of Cas endonuclease to the ssDNA reporter, producing a steric hindrance effect, which limited the trans-cleavage activity. An ideal density was prepared by 1 μM of ssDNA reporter and identified as $5.2 \times 10^{-14}$ mol/mm$^2$, which created sufficient space for Cas12a to perform collateral cleavage on the electrode surface, providing a sufficient electrochemical signal change and ensuring an excellent detection resolution.

Figure 2E:
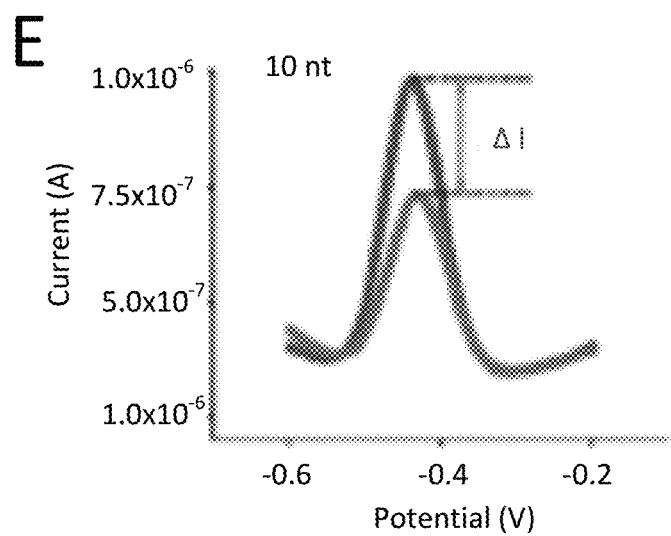
Figure 2F:
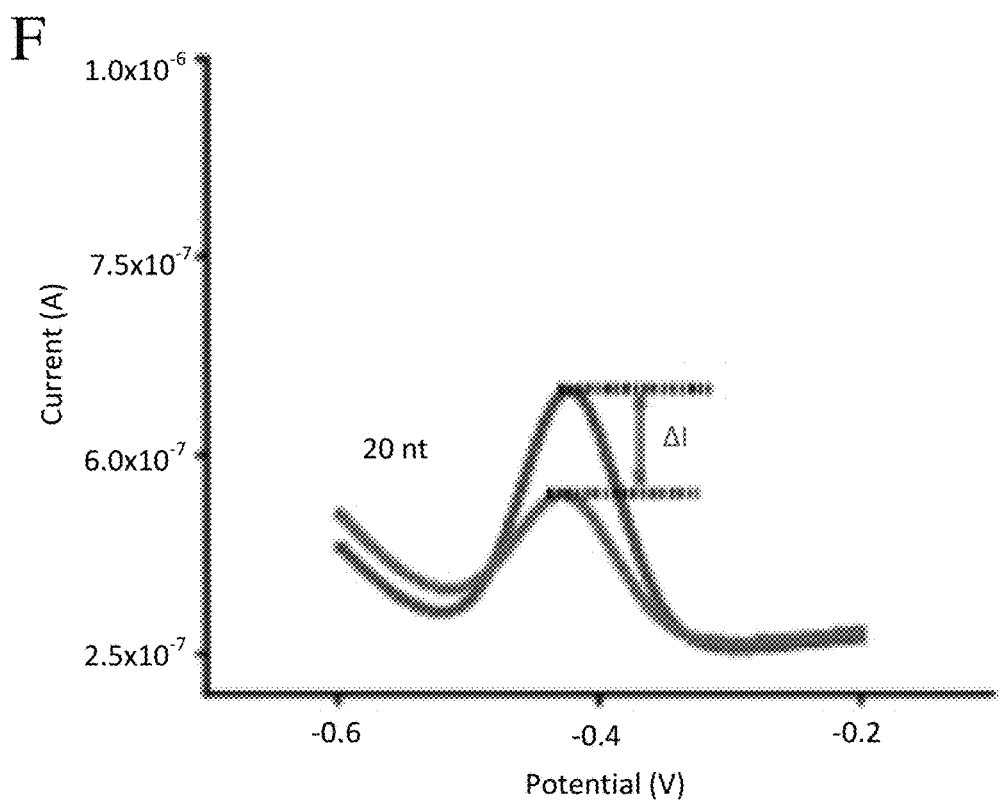
Figure 2G:
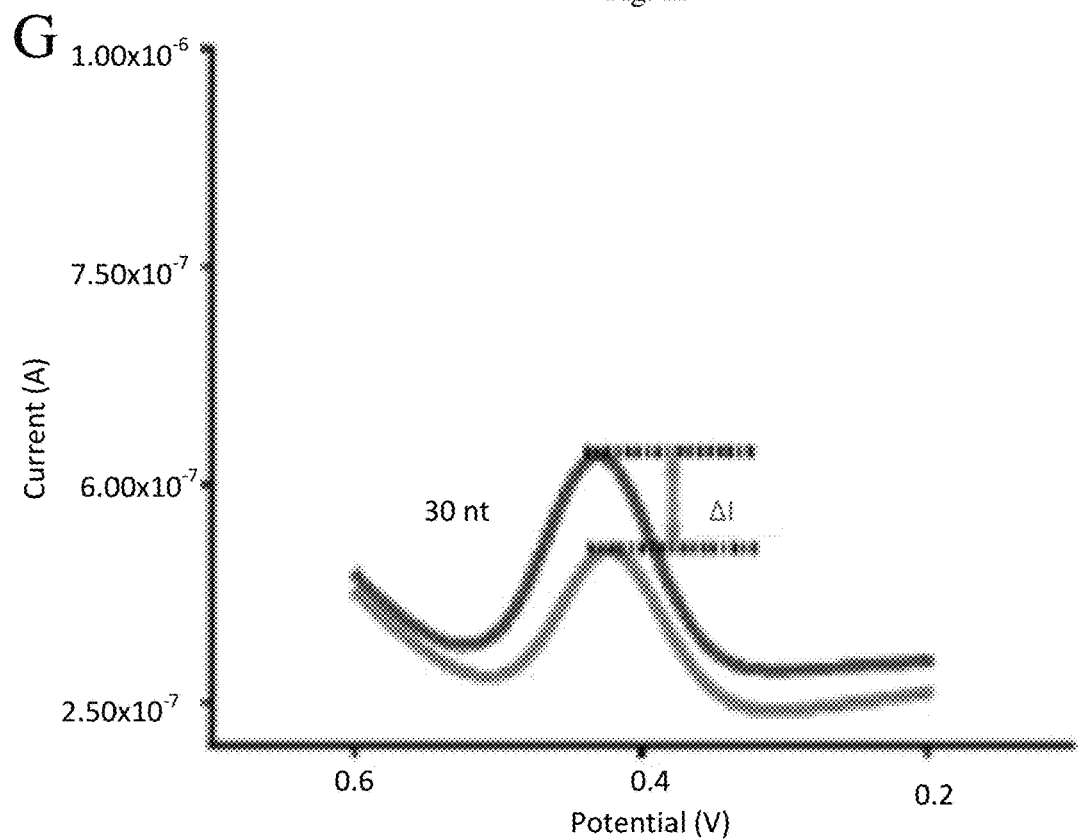
Figure 2H:
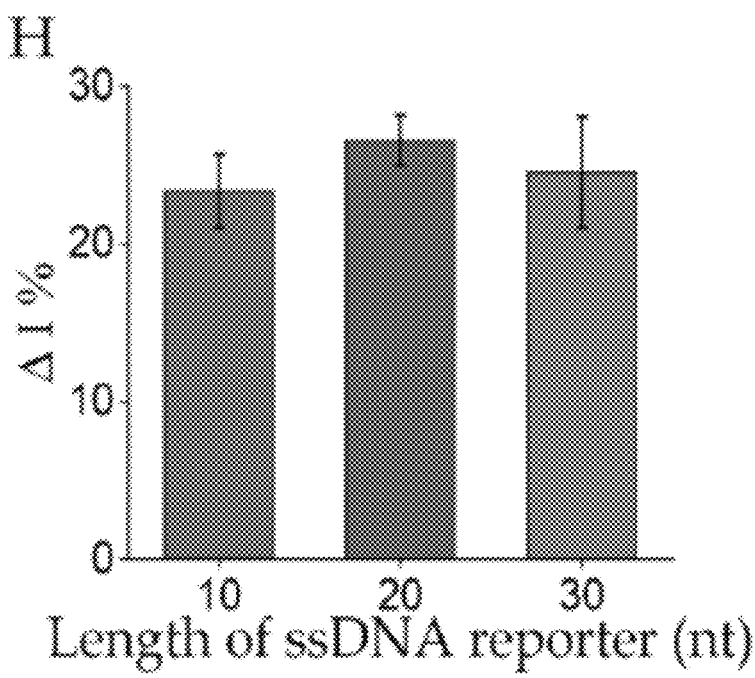

Other than the surface density, the length of the immobilized ssDNA reporter was also evaluated. We hypothesized that ssDNA reporters with different lengths might lead to different cleavage efficiency due to the exposed length difference. Different lengths of ssDNA probes at the same concentration were evaluated based on the same reaction condition of E-CRISPR as investigated previously. Moreover, the effect of passivation agents with different carbon chain lengths may influence the electrostatic interaction between the phosphate backbones of ssDNA probes, therefore was also evaluated for optimized cleavage activity. The selected ssDNA and passivation agent pairs were then compared through the effect of lengths on trans-cleavage activity. However, different lengths of ssDNA reporter only produce a minute variation (<5%) of signal change (FIG. 2H). We observed that for a short ssDNA reporter (10 nt), the electrochemical oxidation current over the background current was larger than that of long ssDNA strand because of its short contact mediated electron tunneling distance to the electrode resulting a faster charge transfer kinetics (FIG. 2E). Therefore, the short probe possessed a large baseline current. As for long reporters (20 nt & 30 nt), they gave a relative low background current (FIGS. 2F&G), but the ΔI % of these long reporters were comparable to that of short reporter. 20 nt ssDNA reporter was selected for further application because of its relative greater degree of signal change and smaller standard error (FIG. 2H). With the completion of the surface packing optimization, we tested the storage stability of the optimized packing of ssDNA electrode by storing in 4° C. at a humidified environment. A stable SWV signal was retained for around 3 days, which is a sufficient turnaround time for clinical point-of-care routine. If a longer storage stability is needed, a multi-component monolayer system can be applied as demonstrated previously to maintain a high-sensitivity over months. Moreover, evaluation of a multi-component monolayer system (e.g., ternary self-assembled monolayers) might also be a potential solution for future researches seeking for a higher sensitivity through tuning the surface molecular packing condition.

Another interesting finding regarding to the cleavage accessibility is that Cas12a-crRNA based trans-cleavage activity is also significantly concentration dependent as was its analog Cas9. Different concentrations of Cas12a-crRNA in response to a same target concentration were evaluated. A high concentration level (>100 nM) in a 30 μL sample solution significantly decreased the activity of the Cas12a nuclease to nonspecific ssDNA reporter, due to that the large size of the Cas12a probably cause a diffusion hindrance effect in the solution. Hence, a relative minor change of current outputs was observed based on a high concentration level of Cas12a-crRNA. An optimized concentration for Cas12a-crRNA duplex trans-cleavage operation was identified to be 30 nM in a 30 μL solution.

E-CRISPR on Nucleic Acid Detection

Figure 3A:
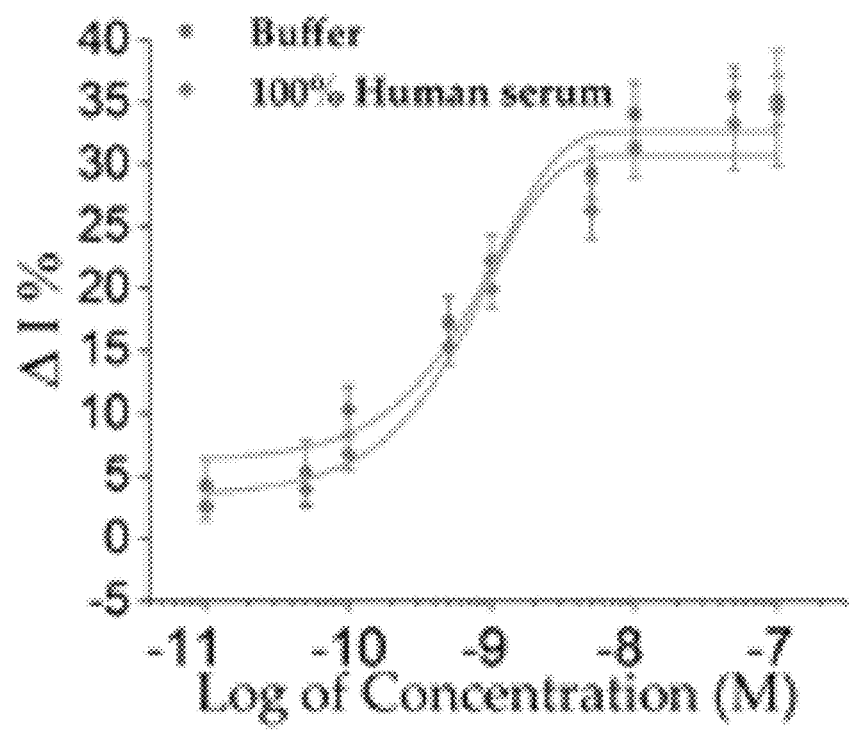
FIGS. 3(A-D) illustrate E-CRISPR analysis of HPV-16. A) Dose-response curve of the detection of HPV-16 in different matrixes (green line—10 mM Tris buffer containing 50 mM NaCl and 15 mM MgCl2; purple line—100% human serum). B) Selectivity study through comparison of the signal changes based on non-target nucleic acids (500 nM) with that of 1 nM of HPV-16 (n=3, *P<0.01, target signal vs. non-target signal). C) Target strands with mismatches at different positions, including PAM region and crRNA complement at different positions: 1, 6, 11, 16. D) Evaluation of the influence of mismatches at different positions on the E-CRISPR signal. A target concentration of 1 nM was applied for all the targets (wild type (WT) and mismatched targets).

Based on the optimized trans-cleavage condition, we evaluated the E-CRISPR platform on the detection of HPV-16. A broad dynamic range (pM to μM) of more than three orders of magnitude was achieved with an IC50 value of 0.78 nM based on the samples prepared in the buffer solution (FIG. 3A). The dose-dependent response curve demonstrated an average standard error (SE) of 2.16% (n=3), indicating a reliable reproducibility. An experimental limit of detection (LOD) at 50 pM was obtained. Worth mentioning, this LOD of optimized trans-cleavage activity based E-CRISPR surpassed previously demonstrated LOD for non-enzymatic amplified nucleic acid detection over two orders of magnitude. Moreover, the detection performance in complex matrix was also evaluated. An IC50 value in pooled human serum was 0.68 nM, which was comparable with the IC50 value (0.78 nM) in buffer solution, indicating a great potential of E-CRISPR in direct analyzing of biological sample. We also tested the effect of target length on the trans-cleavage signal by increasing the length of HPV-16 targeting sequence from 40-mer to 100-mer in the L1-encoding region. Comparing with the detection performance of 40-mer DNA target, 100-mer DNA target presented a similar IC50 value (0.62 nM), indicating that the length of the target would not interfere with the in vitro trans-cleavage activity of Cas12a.

To evaluate the generality of the detection strategy, we further challenged the E-CRISPR system to detect ssDNA erthrovirus, Parvovirus B19 (PB-19), which is known to cause erythema infectiosum in children and pregnant women. A dynamic detection range from pM to μM was achieved with an IC50 value of 0.60 nM. The percentage of signal change was similar to that of detection performance by HPV-16, indicating the on-chip trans-cleavage activity would not be affected by different targets.

Figure 3B:
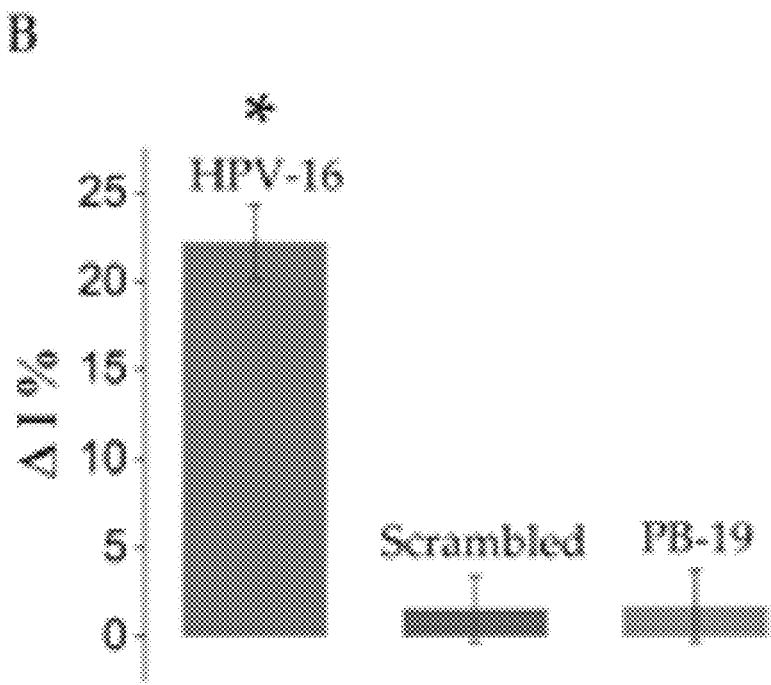
Figure 3C:
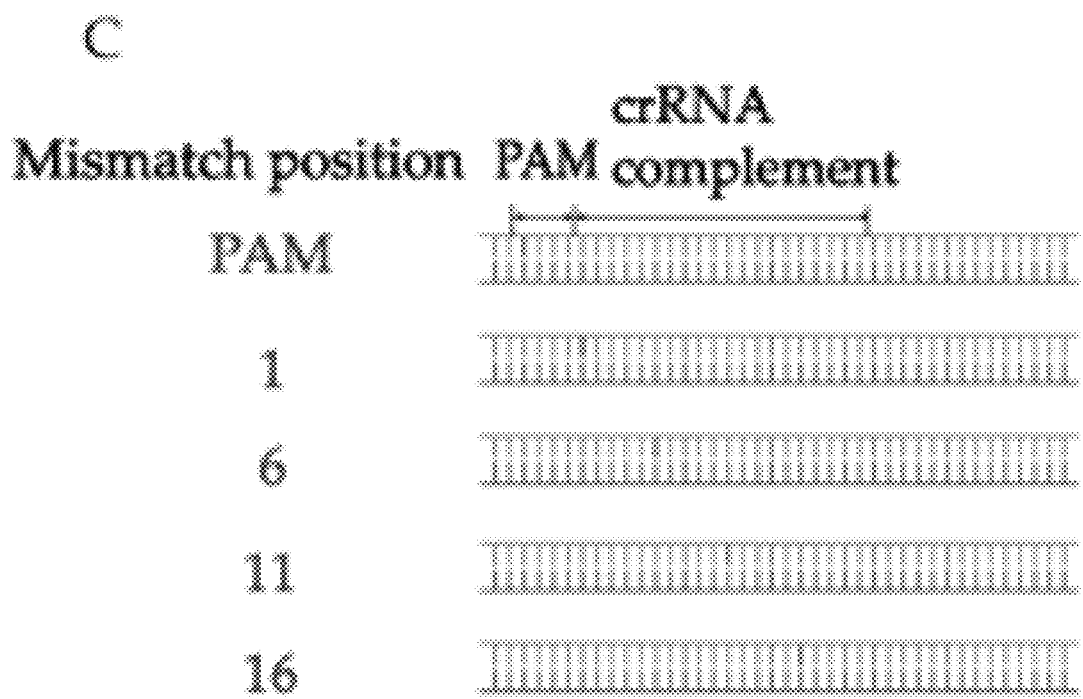
Figure 3D:
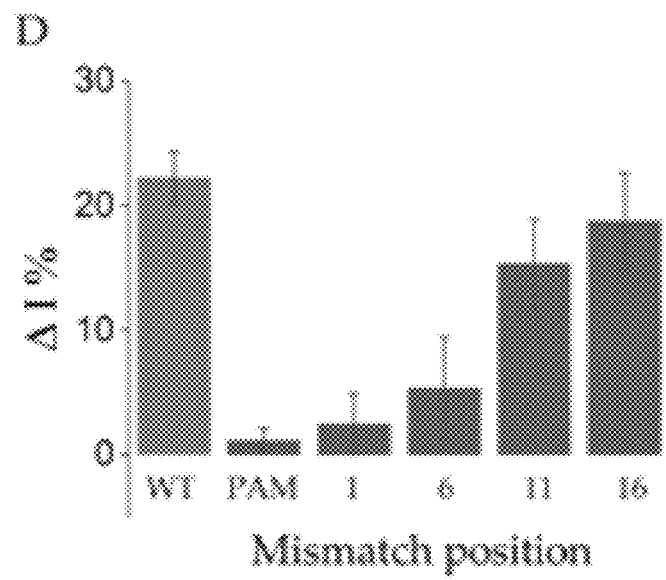

We further investigated the accuracy of the E-CRISPR platform. A scrambled sequence and PB-19 were applied to evaluate the selectivity for HPV-16 detection. 500 nM of scrambled sequence and PB-19 sequence demonstrated a signal change less than 1.5% and 1.7%, which were lower than the standard error of the signal generated by 1 nM HPV-16 target, indicating a good selectivity of the Cas12a-crRNA duplex on differentiating HPV-16 from non-target (FIG. 3B). Selectivity test was also performed for PB-19 detection using HPV-16 and scrambled sequence as interferences, demonstrating the reliable recognition activity of CRISPR system. Furthermore, as a biosensing platform, discrimination of mismatches in the nucleic acid base pairs is of especially importance for the potential application for the identification of disease related point mutations. Thus, we next challenged the E-CRISPR with artificial mismatched nucleic acid targets (HPV-16). The recognition mechanism of CRISPR-Cas12a involves the identification of PAM region on the target to unwind the DNA target by Cas protein and further hybridization between the crRNA and the target strand. Therefore, we designed the mismatches at different positions on the target (FIG. 3C). E-CRISPR signal was obtained based on the detection of 1 nM of these artificial targets (FIG. 3D). Comparing with the wild type (WT) HPV-16 sequence, mutations in PAM region and PAM-adjacent region (position 1) led to complete diminishment of the trans-cleavage signal. This phenomenon indicates the mandatory requirement of PAM sequence for the Cas12a-crRNA duplex to recognize and cleave the target. Moreover, mismatches in the complementary region of crRNA and target demonstrated retarded trans-cleavage activity, consistent with previous mismatch tolerance study of Cas12a. The clear differentiable SWV signal between mismatches at different positions also suggests that the trans-cleavage activity of Cas12a might be utilized to identify the position of the mismatched base pairs as a biosensing strategy. Overall, the developed E-CRISPR demonstrates a sensitive, generalized and cost-effective platform for nucleic acid analysis.

Aptamer Based E-CRISPR Cascade for Protein Detection

Figures 4A, 4B:
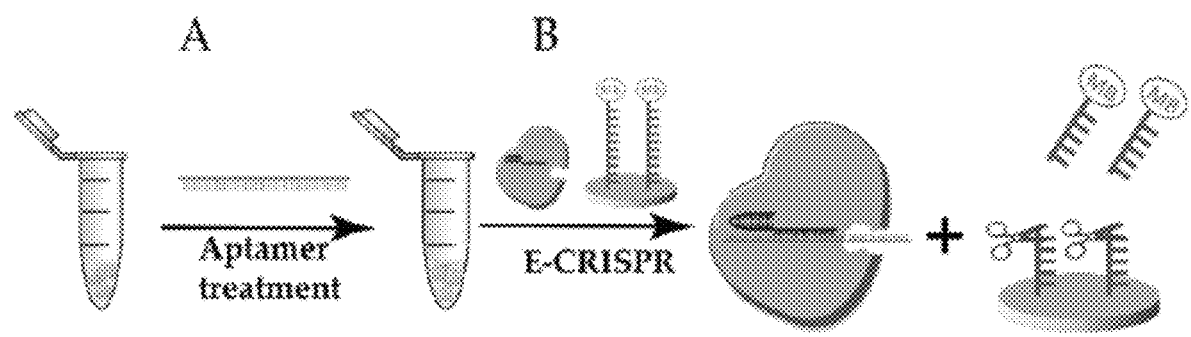
FIGS. 4(A-F) illustrates E-CRISPR cascade for protein detection. A) Sample containing protein target of interest is firstly treated by a fixed concentration of target specific aptamer (ssDNA). B) A E-CRISPR system is specifically designed for the recognition of the aptamer. The remaining concentration of aptamer is analyzed by E-CRISPR. C) A representation of SWV results based on the with target and without target condition. D) Linear calibration curve of TGF-β1 protein detection with an equation of Y=0.91X+1.79 and R-square value of 0.99 (n=3, SE=1.54%). E) Selectivity study through comparison of the signal outputs based on non-target proteins (10 nM) with that of 10 nM of TGF-β1 (n=3, P<0.01 versus different interference substances). F) Concentration-dependent signals observed within conditioned medium harvested at two time-points during the chondrogenic differentiation program of human mesenchymal stem cells (hMSCs) containing TGF-β1. The samples were analyzed by three sets of individual experiments using three different sensors (n=3, *P<0.05, Day 28 vs. Day 2). The horizontal black dashed line represents the average signal variation (n=3) based on the presence of blank conditioned medium.
Figure 4C:
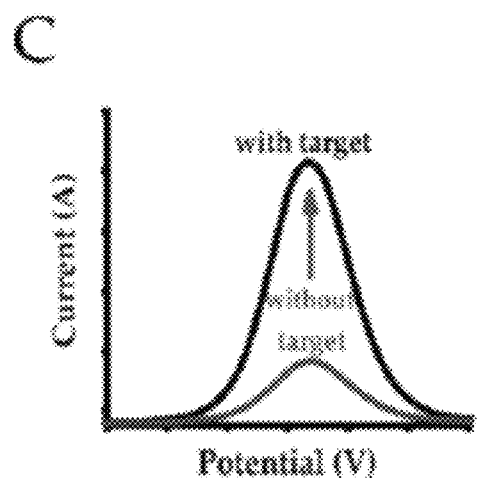

We next explored whether the E-CRISPR could be repurposed as a protein detection platform by utilizing the nucleic acid detection capability of E-CRISPR. For protein detection, ssDNA aptamer was used as the recognition element for a protein of interest. An aptamer based E-CRISPR cascade is designed for protein detection (FIG. 4), which allows the direct analysis of complex sample without any time-consuming processing procedures. A fixed concentration of aptamer is firstly applied to treat the sample directly (FIG. 4A). Cas12a-crRNA is designed to specifically recognize the aptamer. The E-CRISPR is then applied to determine the remaining concentration of aptamer in the sample (FIG. 4B). With the presence of the protein target, less aptamer would be captured and transduced by E-CRISPR, leading to a high electrochemical signal of the methylene blue from the ssDNA reporter. In the absence of the protein target, the electrochemical signal would be lower due to the activation of trans-cleavage activity by the target recognition (FIG. 4C).

Figure 4D:
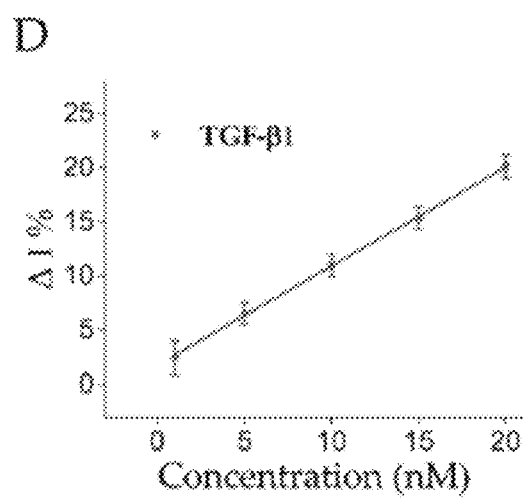
Figure 4E:
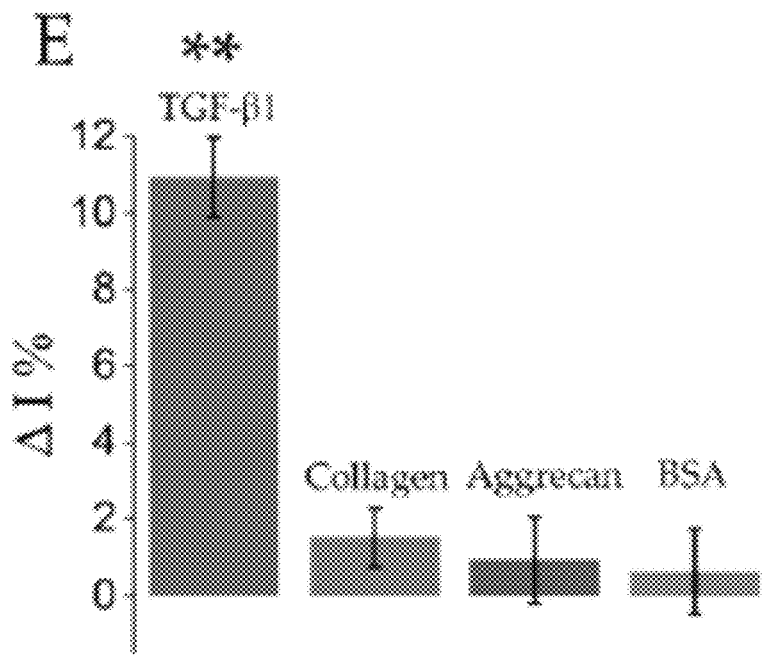
Figure 4F:
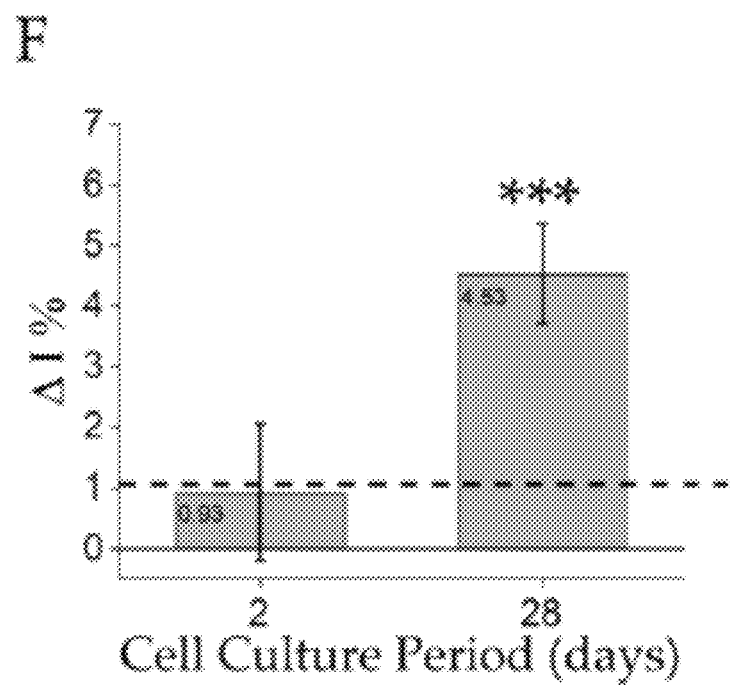

This designed E-CRISPR array was evaluated for the detection of transforming growth factor beta 1 (TGF-β1) protein, which is a secreted protein contributing to cell proliferation and differentiation, and is also recognized as a biomarker for hepatocellular carcinoma. The dose dependent E-CRISPR for the detection of TGF-β1 aptamer was first evaluated based on the previous established trans-cleavage condition. For proof-of-concept, a fixed concentration of aptamer was first applied to treat sample with and without TGF-β1 protein. E-CRISPR was then applied to analyze the samples with and without TGF-β1 protein demonstrating a clear signal difference. In order to increase the detection resolution for nano molar concentration range, a greater degree of current difference between 1 nM and 50 nM is necessary. Therefore, longer trans-cleavage period was investigated to evaluate whether a higher current difference can be obtained due to that the trans-cleavage activity is multiple-turnover reaction. Increasing trans-cleavage period indeed leads to a higher detection resolution, so a trans-cleavage period for protein detection was selected to be 60 min. Therefore, this strategy might be applied to tune the dynamic range and detection limit of the E-CRISPR platform, enhancing the detection performance. An aptamer concentration of 50 nM was selected for protein sample treatment for 30 min. After the treatment, the sample was evaluated by E-CRISPR. A linear detection range was achieved covering three order of magnitudes with an experimental detection limit tested as 0.2 nM (FIG. 4D). The detection specificity was investigated using the conditioned medium from hMSCs chonodrogenesis (a complex matrix) biomolecules, including collagen type II, aggrecan protein and bovine serum albumin. The designed strategy defined a good selectivity on target protein over non-specific molecules, indicating an excellent specificity of the applied aptamer in the system (FIG. 4E). We further challenged the E-CRISPR platform with samples obtained during the chondrogenic differentiation program of hMSCs, which were cultured in aggregates with complete chondrogenic differentiation medium for 4 weeks. TGF-β1 protein was produced during the chondrogenic differentiation process. A clear difference was identified between the conditioned medium obtained at day 2 and day 28 (FIG. 4F). These results are in agreement with the transcriptome analyses performed during Hmsc chondrogenesis of the same analyzed sample, indicating a reliable performance of the designed E-CRISPR array for protein detection. The nucleic acid based receptor is a generalized recognition element for both protein and small molecule. Hence, the designed E-CRISPR array can also be extended to a wide variety of analytes.

Example 2

In this Example, we construct a CRISPR array initiated cell-free genetic circuit. The CRISPR array identifies specific biomolecular sequences as inputs and the CRISPR processing results dsDNA overhangs, initiating a primer exchange reaction (PER) based DNA circuit. The primer exchange reaction performs autonomous synthesis of prescribed DNA oligos, translating the molecular cues into an arbitrary sequence, which can be further cascaded and quantitatively amplified based on the same oligo synthesis mechanism. The whole genetic circuit is operated under a simple Boolean logic design principle. To evaluate the applicability of the integrated multi-function circuit, we implemented this molecular network abstraction into a bioanalytical system operating on an electrochemical interface, which serves as a simple and cost-effective transduction system, capable of rapidly curating molecular information and transducing into data.

Bioanalytical strategies have been extensively developed toward better sensitivity, simplicity and selectivity, while valid strategies can be further integrated into a portable, cost-effective, rapid transduction platform for an ideal point-of-care system. So far, a high-resolution molecular analytical strategy, capable of differentiating infinitesimal concentration variation, which is essential to understand the critical threshold limit of biomolecules, has not been realized with a simple biosensing system. For high-resolution molecular analysis, the biomolecular signal is necessarily amplified downstream through centralized equipment or delicately fabricated nano-devices, limiting the general applicability. Here, we show the capability of the multi-function biochemical circuit as an upstream biological processor which 1) identifies a specific genome sequence, 2) transforms the double-stranded gene into a structure that can be accessed for circuit wiring, 3) translates the input sequence into an arbitrary output, 4) amplifies the arbitrary output sequence into a concatemer, achieving a one-to-multiple turnover reaction cascade and therefore delivering an analytical construction possible to differentiate minute concentration change. The resulted molecular output is further probed by a downstream single-use electrochemical sensing array, providing a rapid analytical result. As a proof-of-concept, we challenged this multi-function biochemical circuit based electrochemical biosensing system on analyzing the genome of the 2019 novel coronavirus, Severe Acute Respiratory Syndrome-related Corona-virus (SARS-CoV-2) in complex human sample.

Results and Discussion

The design and operating principles of the multi-function heterogeneous biochemical circuit are shown in FIG. 5A.

Figure 5C:
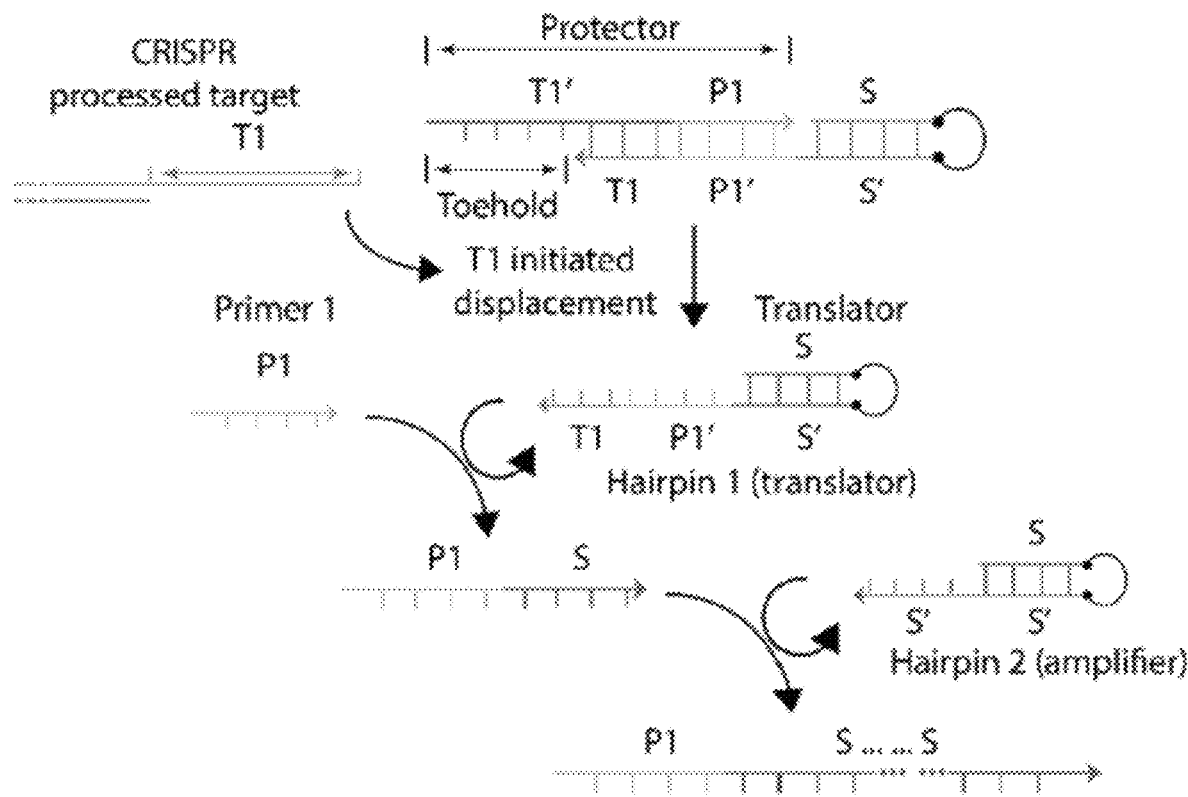
FIGS. 5(A-D) illustrate modular construction of multi-function heterogeneous biochemical reaction circuits. A) A multi-function heterogeneous biochemical circuit constructed by paired CRISPR system and primer exchange reaction, processing genetic information and translating into electric signal. B) Guided by two offset sgRNAs, a pair of CRISPR Cas9 D10A nucleases target opposite sequence on the gene target, transforming the intact dsDNA into a 3'-overhang strand available for cascading circuit. (Blue triangle: cleavage position; Yellow box: PAM region). C) Primer exchange reaction mediated translator and amplifier. A protector gated hairpin 1 serves as a translator, only functioning with the pre-sence of the gene target. An arbitrary sequence (S) is stored in the nascent strand (P1-S) elongated by hairpin 1. Hairpin 2 serves as an amplifier and catalyses the extension of P1-S with repetitive sequence S, forming a concatemer. D) The output of the heterogeneous bio-chemical circuit is examined by an electrochemical biosensing platform. A capture strand is tethered on the electrode to probe any synthesized concatemer. A signaling probe containing an electrochemical tag, complementary to the repetitive sequence S, binds to the concatemer and generates electrochemical signal.
Figure 5D:
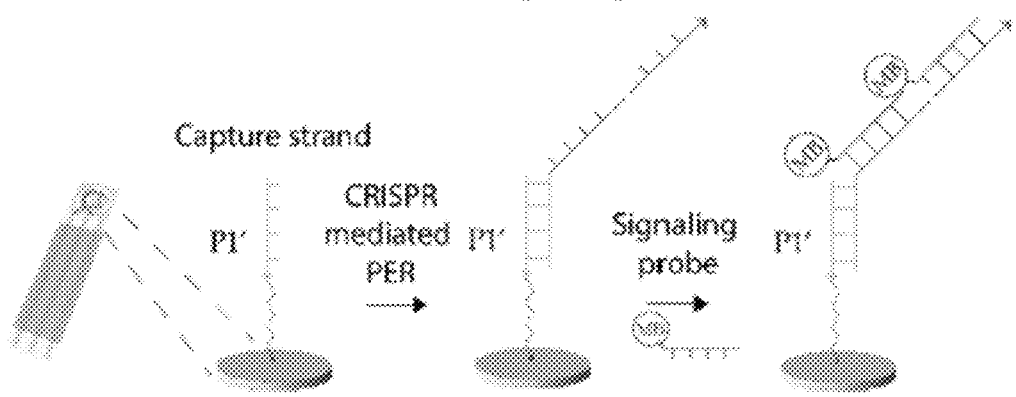

First, in order to activate the biochemical circuit, a specific gene target as the circuit input is identified through the processor element, in which a programmable RNA-guided ribonucleoprotein, clustered regularly interspaced short palindromic repeats (CRISPR) Cas9, is applied as the recognition element, owing to its high-specificity and complementarity dependent cleavage nuclease activity. The capability of CRISPR to directly examine a double-stranded target is de-pendent on the recognition of a specific protospacer adjacent motif (PAM) sequence (5'-NGG) by Cas9, which activates the Cas9 nuclease to unwind the dsDNA and allows the single-guide RNA (sgRNA) to invade and further evaluate the sequence complementarity. With the confirmation of the sequence complementarity, an exact structural conformation formed by target-sgRNA-Cas9 results the cleavage activity on the target. However, conventional Cas9 nuclease creates a blunt cut on the dsDNA, which does not provide any accessibility to the sequence information of the cleaved strand and therefore hindering the utilization of target in-formation for cascading circuit. In order to acquire molecular information from the target upon the identification by CRISPR, a Cas9 D10A mutant nickase, which cleaves only the binding strand of the sgRNA, is utilized with a pair of offsets sgRNAs targeting opposite strands to transform the dsDNA structure, providing a 3'-overhang (T1) that can be accessed and utilized as a molecular input for downstream circuit (FIG. 5B). In order to discriminate minute concentration change, a one-to-multiple turnover amplification is necessary for the CRISPR processed target. Instead of directly amplify the target information processed by the Cas9 D10A nickase, in order to enhance the generality of this heterogeneous circuit, a translator element is applied to translate the target sequence into an arbitrary sequence first, dis-connecting the sequence information between the output and the input, which makes the amplification element generally applicable to any sequence of interest. Primer exchange reaction (PER), an autonomous mechanism for synthesis of nascent single-stranded DNA, is utilized as the molecular reaction pathway for translator and amplifier elements (FIG. 5C). The molecular mechanism of PER on synthesis of ssDNA mainly relies on a primer, a catalytic hairpin substrate and a displacement polymerase. The 3' end exposed region of the hairpin substrate allows the binding of the primer. The stem region of the hairpin is a prescribed sequence for the extension of the primer. A strand-displacing polymerase is applied to copy the stem region and halted at a stop sequence before the loop region. The nascent strand is then released from the catalytic hairpin through a three-way branch migration process. In order to utilize the target information processed by CRISPR as an initiation signal for downstream PER reactions, a protector (T1'-P1) is designed to cover the primer binding region (P1') on the catalytic hairpin 1 with an exposed toehold region, which is complementary with the 3' overhang target region (T1). Therefore, only with the presence of the paired Cas9 D10A processed target, the protector can be released from the hairpin 1 through a strand displacement reaction, making the primer binding region available and cascading the biomolecular reactions. Primer (P1) binds to the P1', extended by a BST Large fragment DNA polymerase and followed by the three-branch migration, producing an elongated P1-S strand. The sequence design of S strand can be arbitrary and in our case, we design the S strand without guanine. Therefore, only dATP, dCTP and dTTP are necessary for the synthesis of this nascent strand, allowing us to simply put the stop codon as guanine at the position close to the loop region. Till now, the target information is translated and stored into an arbitrary sequence S. In order to amplify the signal of the target, a second hairpin, known as the telomerase hairpin, utilizing the same sequence for primer binding region and the copying region, is applied to grow a concatemer (P1-S-.-S) with repeated sequence chained together through multiple-turnover primer exchange reaction on the same strand. The concatemer is the amplified product serving as the signaling strand for signal transduction based on the multiple S strands. Finally, to acquire the molecular information, a micro-fabricated electrochemical single-use sensing array is applied to transduce the molecular signal into physicochemical signal through electrochemistry (FIG. 5D). In order to probe the molecular signal through the output elongated concatemer, a surface capture strand modified with a thiol group (SH-P1'), tethered on the gold working electrode through Au—S bond, is complementary to the primer sequence. Therefore, any primer, either going through the biochemical circuit or not, can be captured onto the sensor. A signaling probe (S'-MB), complementary to the signaling strand (S) and containing a methylene blue electrochemical tag, is further introduced into the system. Only with the presence of the signaling concatemer, multiple copies of signaling probes can be hybridized onto one concatemer generated by one copy of target originally, amplifying the electrochemical signal.

Figure 6A:
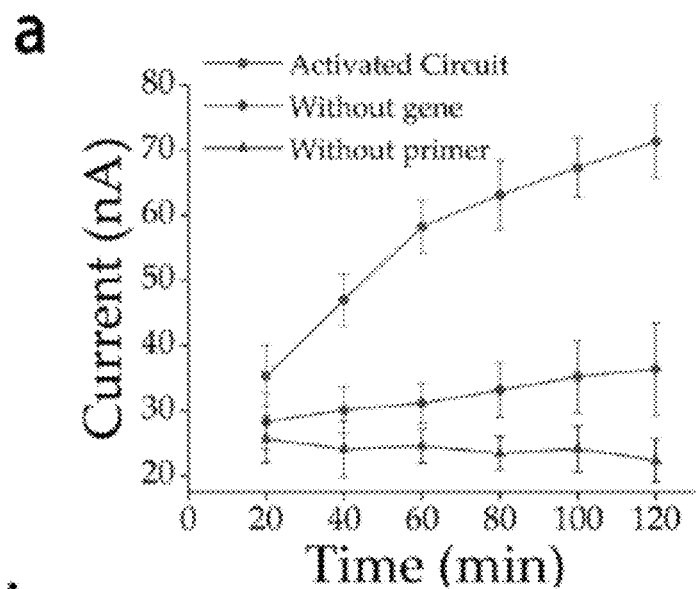
FIGS. 6(A-D) illustrate proof of concept evaluation of the electrochemistry transduced biochemical circuit. A) Time-dependent electrical outputs based on activated circuit, negative control (without gene and without primer). B) A typical square wave voltammetry (SWV) graph showing the electrochemical currents of 1) fully activated circuit with primer (final concentration of 100 nM) and gene (final concentration of 50 nM); 2) non-activated circuit without gene (blue) or without primer (black). C) The Boole-an AND conjunction dependent circuit elements. CRISPR processor is operated as a 3-input AND gate. PER based translator and amplifier elements are operated as a 4-input AND gate. D) Comparison of the performance of the integrated circuit through electrochemical signal gain %=(peak current-baseline current [without primer condition])/baseline current). Each input element was investigated based on the Boolean logic. *P<0.01; **P<0.05 (signal of fully operated circuit against signal of incomplete circuit). The bar represents the mean value of three orthogonal repeats. The error bar represents ±SE.
Figure 6B:
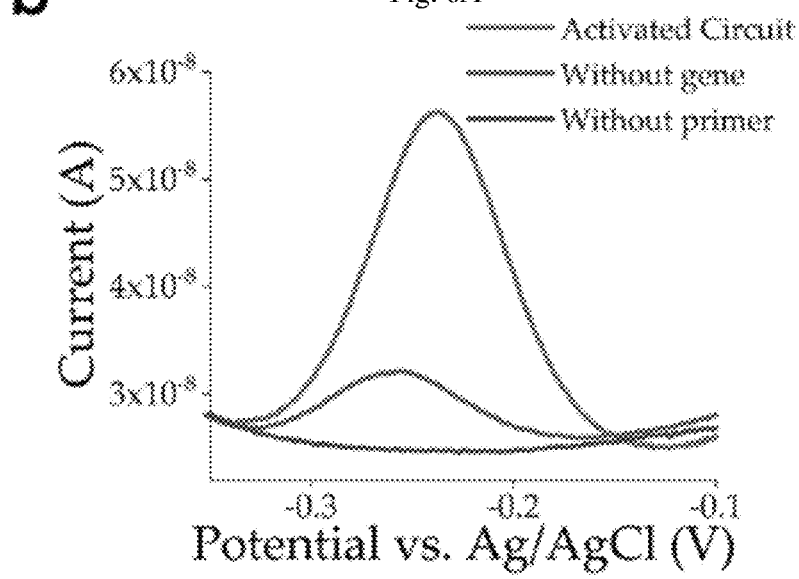

We first evaluated the feasibility of the whole biochemical circuit operation workflow through electrochemistry. The biochemical circuit was examined based on the presence or non-presence of two critical input molecules, target gene (Genebank No. LC528233.1, region 28350-28530) and primer. Square wave voltammetry (SWV) was applied for electrochemical analysis after quenching the reactions by washing out the reactants from the sensor surface. After CRISPR processing, a time-dependent evaluation was conducted to select a reaction period of PER in order to generate substantial electrochemical current difference for the fully activated circuit over the two control conditions (lack of critical inputs). A clearly differentiable signal above the background and leakage signal can be identified through electrochemistry after 20 min (FIG. 6A). Considering the stability of signal-to-noise ratio (signal gain) and the time-efficiency for bioanalytical application, a 1 h reaction period was selected for further evaluation. A typical SWV signal demonstrated the current outputs of the activated circuit (red) with all components and the non-activated circuit lack of the primer (black) or the gene input (blue) at 1 h time point (FIG. 6B), indicating a good integrity and performance of the heterogeneous biochemical circuit.

Figure 6C:
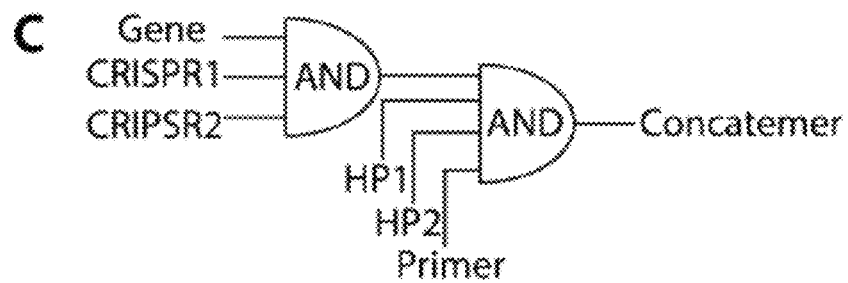
Figure 6D:
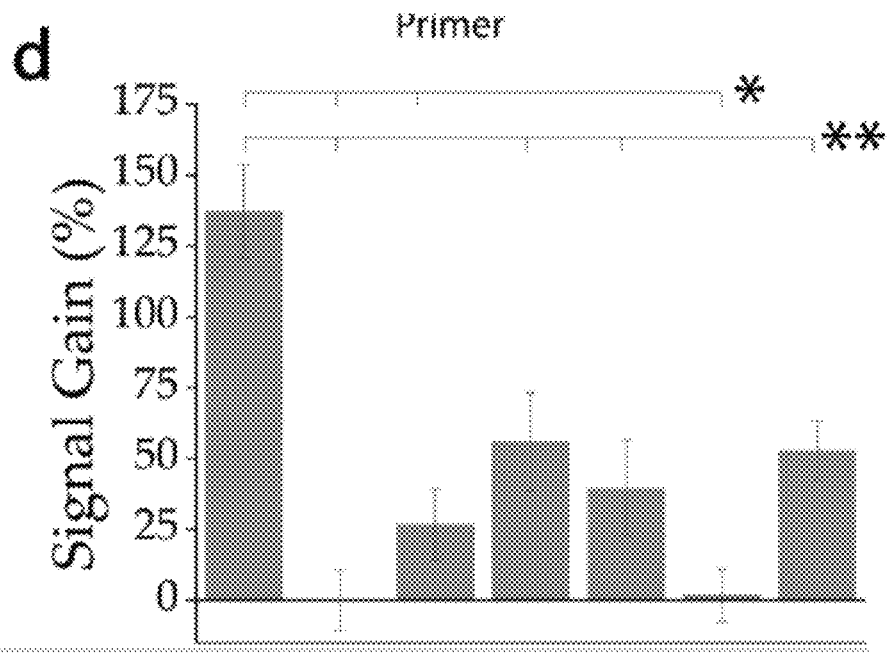

Logic AND conjunction gate is the foundation of the circuit architecture. Hence, we further evaluated the separate functionality of each circuit element based on Boolean logic (FIG. 6C). The electrical signal was normalized with the baseline signal based on the absence of the primer condition, which fully shuts down the pathway for concatemer synthesis, therefore no observable electrochemical signal of methylene blue as shown by the black line in FIG. 6B. A significant signal gain was observed comparing the output signal of fully activated circuit with that of any incomplete circuit (FIG. 6D). The CRISPR array based processor element is operated as a three-input AND gate. Lack of any input in this gate leads to a significant decrease of signal comparing with that of fully operated circuit. A stable leakage reaction (FIG. 6B and FIG. 6D) was observed as typically found in a gene circuit, but the leakage resulted output signal was not statistically significant in our case. We further noticed that the signal output in which Cas-sgRNA1 was not present was slightly higher than the signal output in which Cas-sgRNA2 was not present. We suspected that this phenomenon is due to the different cleavage site of sgRNA1 and sgRNA2. The cleavage site of sgRNA2 potentially exposes the target sequence (T1), which might increase the possibility to activate the downstream PER element, indicating the importance of accessibility of target information in a biological circuit. Afterwards, the PER based translator and amplifier elements can be integrated as a four-input AND gate. Lack of primer fully turns off the PER reaction therefore the whole translator and amplifier are bootless. Lack of hairpin1 results no direct sequence information connection in the circuit, removing the capability to translate the target into signaling strand. Lack of hairpin2 leads to no formation of the concatemer, therefore removing the capability to amplify the signal. The evaluation based on the Boolean AND function firstly confirms the feasibility of this integrated construction concept and further demonstrates the integrity, functionality and modularity of this electro-chemistry transduced heterogeneous multi-function bio-chemical circuit.

Figure 7A:
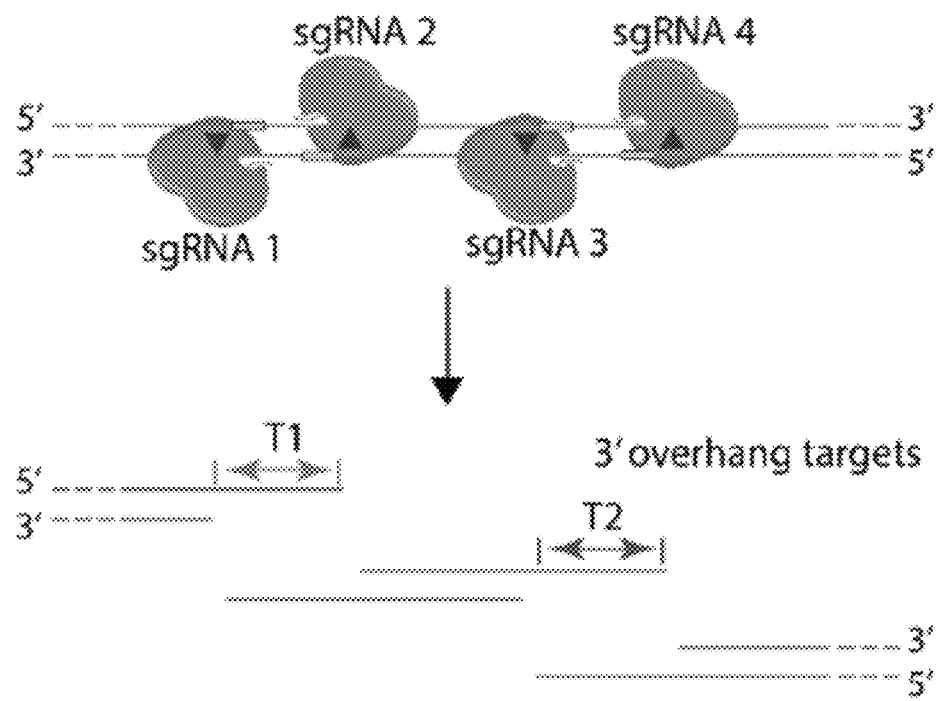
FIGS. 7(A-D) illustrate two-pair CRISPR processed target gene multiplexed signaling pathway. A) Four separate sgRNAs direct four Cas9 D10A nucleases to adjacent target sites, transforming the target into three fragments containing two distinct 3' overhangs accessible for molecular cascading. B) Two orthogonal translator hairpins are initiated by available target sites resulted from CRISPR processing. Target information is translated into an arbitrary sequence, which is further integrated into the same amplifier hairpin, producing a signaling concatemer. C) Compari-son of signal gain between single signaling pathway and multiplexed signaling pathway based on different concentrations of gene input. Signal gain %=(peak current-baseline current [without gene condition])/baseline current). D) A dose-dependent electrochemical response of in-tegrated bio-chemical circuit in a range of concentrations of gene in-put. The bar represents the mean value of three orthogonal repeats. The error bar represents ±SE. **P<0.05.
Figure 7B:
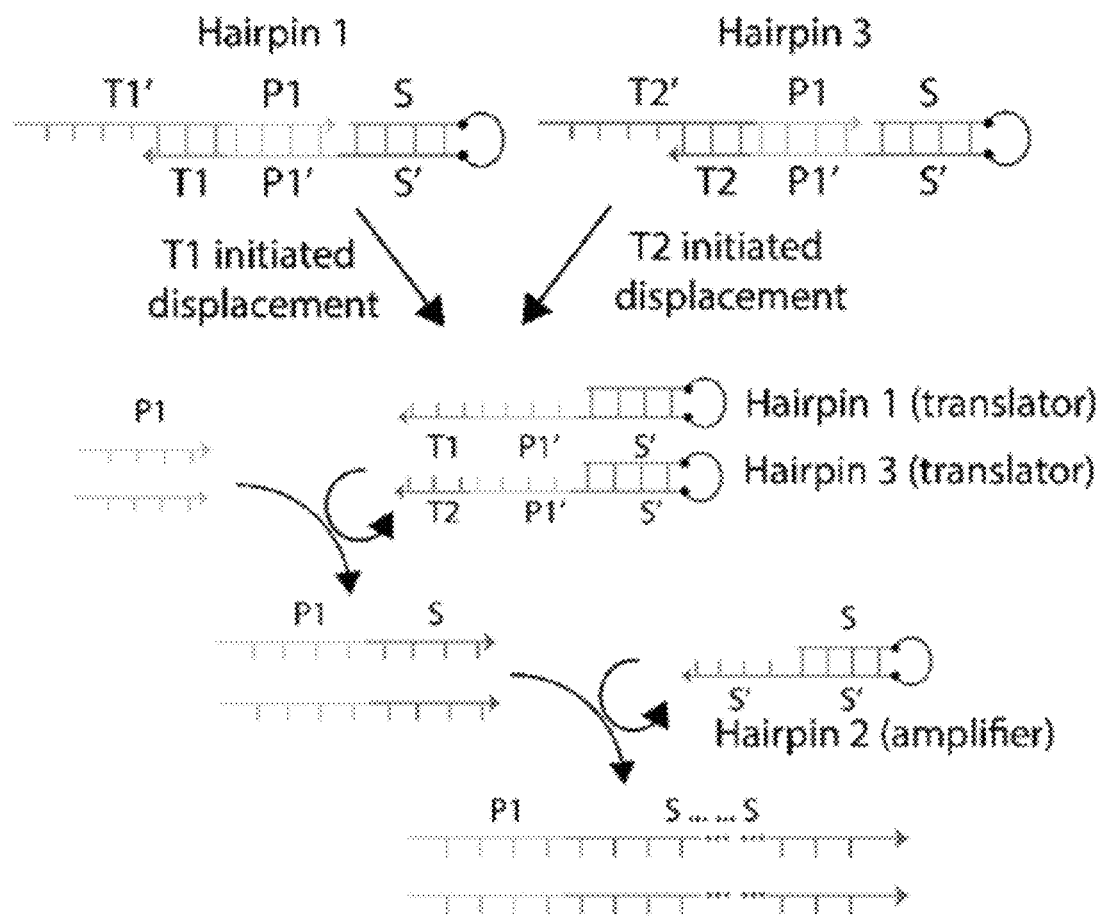

From the perspective of bioanalytical application, the proposed biochemical circuit achieves multiple-turnover amplification of target signal after target identification. We further rationalized that generating multiple defined overhangs on one target can provide multiple opportunities to amplify the target signal, increasing the signal gain. Furthermore, owing to the capability to translate the target in-formation into a prescribed arbitrary sequence, same signaling sequence information can be used to construct the downstream electrochemical signaling scaffold, enhancing the detection resolution. To explore this conceptual possibility, another pair of CRISPR processor is introduced to process the same target. Therefore, two orthogonal 3'-overhangs are available to initiate PER cascades (FIG. 7A). The design principle of multiple offset sgRNAs was applied from a pre-vious study, which demonstrated that multiple cleavage sites can produce a more effective homology directed repair (HDR). The HDR actually holds a similar molecular mechanism regarding the sequence accessibility as what we propose here. Owing to the independence of copying domains in the gated hairpin, toehold design is straightforward and same primer binding sequence can be applied (FIG. 7B), indicating the two overhangs can be translated into the same sequence and further amplifying through the same hairpin amplifier (hairpin2). This design significantly enhances the simplicity and requires a minimal number of DNA operators, minimizing the crosstalk possibility and network complexity. As we previously noticed in FIG. 7C, sequence accessibility can be critical to the efficiency of circuit operation. We suspected that 4 cutting sites can further lead to a greater degree of accessibility of target site due to that the increased number of fragments of the gene target means a higher entropy or a decreased internal energy of each strand, promoting the strand dissociation process after cleavage. After processed by two pairs of CRISPR Cas9 D10A-sgRNAs, the same single PER circuit (as shown in FIG. 6) was conducted to process the target. An increased signal output was observed for two-pair Cas9 D10A-sgRNAs processed target comparing with the signal output based on the condition in which only one pair of Cas9 D10A-sgRNAs was applied, indicating that accessibility of molecular input at the connection gate can be an important factor for the efficiency of biochemical circuit.

Figure 7C:
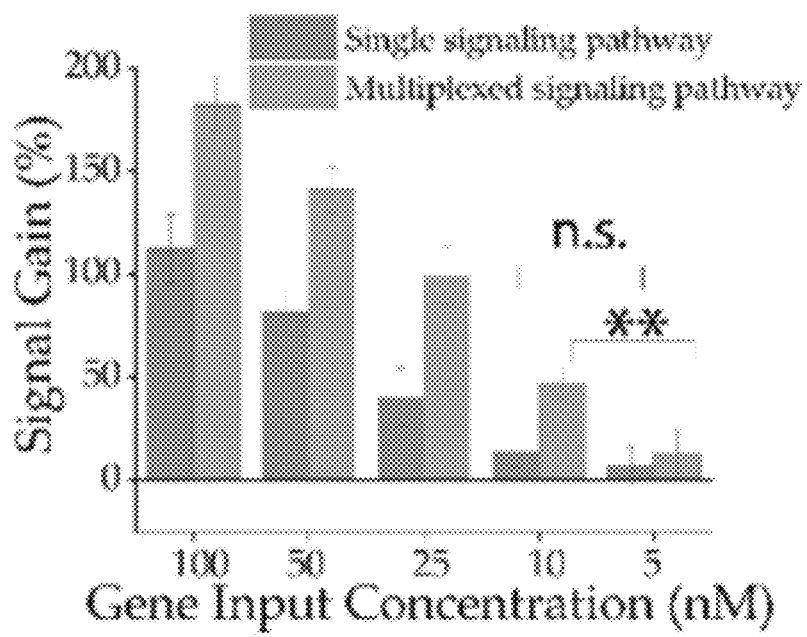

The performance of this two-pair CRISPR mediated multiplexed signaling pathway was compared with previous one-pair CRISPR mediated single signaling pathway (FIG. 7) based on different concentrations of the gene target (FIG. 7C). A higher signal output was observed for multiplexed signaling pathway (FIGS. 3A and B) over the single signaling pathway (FIGS. 1A and B) at multiple concentrations, confirming the principle of this biochemical circuit. Moreover, multiplexed signaling pathway was capable to differentiate concentration difference of 5 nM, which could not be achieved by the single signaling pathway strategy. Furthermore, bioanalytical devices with a higher analytical resolution, indicated by the change of signal between different concentration gradients, can not only minimize the possibilities of false-positive/negative result but also potentially reveal unknown information based on minute concentration change. Therefore, we compared the change of signal based on different concentration gradients between the single signaling pathway and the multiplexed signaling pathway. Over 7-fold increase of analytical resolution was observed for multiplexed signaling pathway over single signaling pathway, proving the resolution enhancement capability of the proposed biochemical circuit.

Figure 7D:
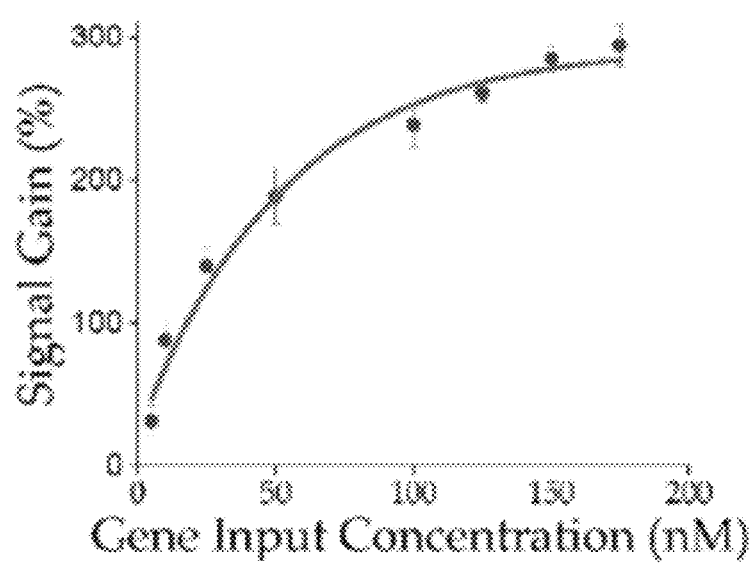

We further aimed to enhance the performance of the biochemical circuit in order to produce a reliable and high-fidelity analytical platform. The original study on PER demonstrated that the increase of the catalytic hairpin concentration and the magnesium ion ($Mg^{2+}$) concentration was able to enhance the kinetics of the primer exchange reaction. We tested these two aspects in our system. Firstly, while maintaining the concentration of primer (800 nM), hairpins (100 nM) and the target gene (50 nM), increasing the con-centration of magnesium ion to 15 mM did increase the signal gain and provide a more stable response. For hairpin concentration, we first evaluated the concentration dependence of the gated hairpin (translator). While maintaining the concentration of primer (800 nM), magnesium ions (15 mM) and the target gene (50 nM), an increase of overall signal output was observed with increased concentration of each gated hairpin, but the increased concentration of gated hairpin also led to a higher background signal resulted by the reaction leakage, therefore the change of signal gain was not discernible. To prevent the signal leakage, we suspected that the increase of the concentration ratio of protector1 and protector3 to hairpin1 and hairpin3 could decrease the reaction leakage. However, increased concentration of protector might also lead to less sensitivity of the analytical application, due to the direct binding of the target strand with the excess free protector in the solution instead of initiating the displacement of bound protector from the gated hairpins. In this context, a low concentration (5 nM) of gene target was used to evaluate the performance to ensure no loss of analytical resolution. A ratio of 1.2:1 of protector over hairpin was selected with decreased leakage signal while maintaining the detection resolution, resulting a higher signal gain. Finally, the effect of concentration of the telomerase hairpin amplifier was evaluated based on the target concentration at 5 nM and an optimized signal gain was identified at a concentration of 250 nM. The property of this hairpin is amplifying signal obtained from the translator hairpins, so it amplifies both the leaky signal and the specific signal, therefore it does not contribute significantly to the normalized signal gain. Based on the optimized experimental condition, a dose-dependent signal response was evaluated in a range of target concentrations (5-200 nM) within a total turnaround time around 1.5 h (FIG. 7D). A plateau was found when the gene concentration was over 150 nM, which might be due to the limited concentration of CRISPR processors in the system. An experimental detection limit was identified around 5 nM, which is a sufficient level for analytical platform to analyze sample after enzymatic amplification treatment. Furthermore, to explore the potential of this sensing strategy, we tried to evaluate the interference of point mutation at different CRISPR targeting region on the signal gain. CRISPR Cas9 has shown outstanding selectivity toward mutations at its PAM region. Therefore, based on our multiple target sites, mutations inside four different PAM regions were designed to evaluate the sensing performance of our biochemical circuit. Signal generated by 50 nM of mutated targets were evaluated and compared with that of wild type target. All mutations demonstrated significant decreases of signal gain comparing with that of wild type. We also observed that single mutation at PAM 2 of sgRNA 2 and PAM 4 of sgRNA 4 contributed greater decrease of signal gain comparing with PAMs of sgRNA1 and sgRNA3. These observations first proved that for the design of biosensing system to differentiate point mutation, recognizing a mutation inside the PAM region is a reliable strategy. Specifically, for our paired CRISPR array, mutations in the PAM regions of the overhang strand (5'-3') inhibit Cas9 recognition and cleavage activities toward the 5'-3' strand, therefore limiting the exposure of the overhanging region to the following DNA circuit. Without the exposed target information, the molecular cue to initiate of the PER cascade is lost, diminishing the overall signal gain.

Figure 8A:
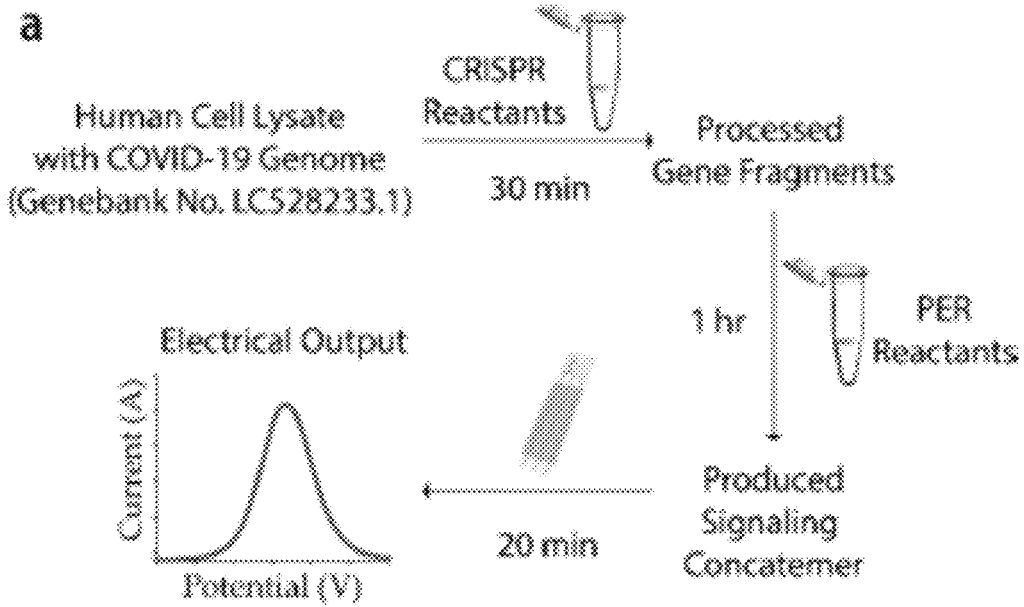
FIGS. 8(A-B) illustrates a modular bioanalytical strategy. A) The modularity nature of the biochemical circuit allows simple construction of individual processes for sample analysis, transforming biomolecule input into electrical output within 2 h. B) Evaluation of the matrix effect of the bioanalytical platform with spiked samples in human cell lysate proved the capability of the platform on complex sample analysis. Interference evaluation based on non-specific gene target (HPV-16) demonstrated the reliable selectivity of the CRISPR mediated recognition process.
Figure 8B:
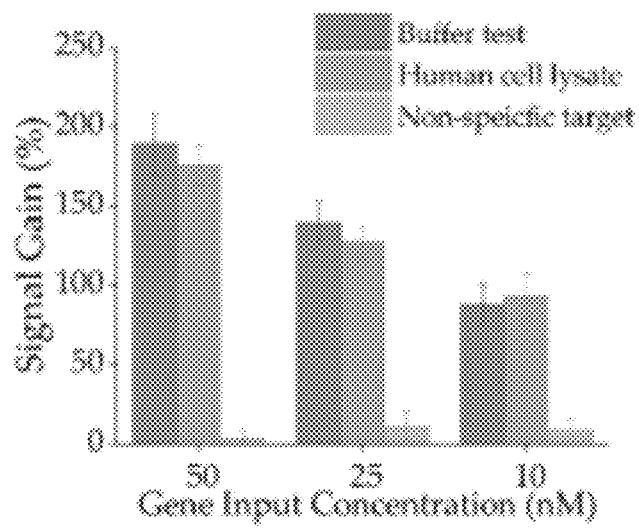

To demonstrate the potential of this electrochemistry transduced integrated heterogeneous biochemical circuit on a realistic bioanalytical application, we challenged this integrated platform with human cell lysates spiked with the synthetic genome fragment of SARS-CoV-2. Owing to the modularity nature of the biochemical circuit (FIG. 8A), the observed for multiplexed signaling pathway over single signaling pathway, proving the resolution enhancement capability of the proposed biochemical circuit.

We further aimed to enhance the performance of the biochemical circuit in order to produce a reliable and high-fidelity analytical platform. The original study on PER demonstrated that the increase of the catalytic hairpin concentration and the magnesium ion ($Mg^{2+}$) concentration was able to enhance the kinetics of the primer exchange reaction. We tested these two aspects in our system. Firstly, while maintaining the concentration of primer (800 nM), hairpins (100 nM) and the target gene (50 nM), increasing the con-centration of magnesium ion to 15 mM did increase the signal gain and provide a more stable response. For hairpin concentration, we first evaluated the concentration dependence of the gated hairpin (translator). While maintaining the concentration of primer (800 nM), magnesium ions (15 mM) and the target gene (50 nM), an increase of overall signal output was observed with increased concentration of each gated hairpin, but the increased concentration of gated hairpin also led to a higher background signal resulted by the reaction leakage, therefore the change of signal gain was not discernible. To prevent the signal leakage, we suspected that the increase of the concentration ratio of protector1 and protector3 to hairpin1 and hairpin3 could decrease the reaction leakage. However, increased concentration of protector might also lead to less sensitivity of the analytical application, due to the direct binding of the target strand with the excess free protector in the solution instead of initiating the displacement of bound protector from the gated hairpins. In this context, a low concentration (5 nM) of gene target was used to evaluate the performance to ensure no loss of analytical resolution. A ratio of 1.2:1 of protector over hairpin was selected with decreased leakage signal while maintaining the detection resolution, resulting a higher signal gain. Finally, the effect of concentration of the telomerase hairpin amplifier was evaluated based on the target concentration at 5 nM and an optimized signal gain was identified at a concentration of 250 nM. The property of this hairpin is amplifying signal obtained from the translator hairpins, so it amplifies both the leaky signal and the specific signal, therefore it does not contribute significantly to the normalized signal gain. Based on the optimized experimental condition, a dose-dependent signal response was evaluated in a range of target concentrations (5-200 nM) within a total turnaround time around 1.5 h (FIG. 7D). A plateau was found when the gene concentration was over 150 nM, which might be due to the limited concentration of CRISPR processors in the system. An experimental detection limit was identified around 5 nM, which is a sufficient level for analytical platform to analyze sample after enzymatic amplification treatment. Furthermore, to explore the potential of this sensing strategy, we tried to evaluate the interference of point mutation at different CRISPR targeting region on the signal gain. CRISPR Cas9 has shown outstanding selectivity toward mutations at its PAM region. Therefore, based on our multiple target sites, mutations inside four different PAM regions were designed to evaluate the sensing performance of our biochemical circuit. Signal generated by 50 nM of mutated targets were evaluated and compared with that of wild type target. All mutations demonstrated significant decreases of signal gain comparing with that of wild type. We also observed that single mutation at PAM 2 of sgRNA 2 and PAM 4 of sgRNA 4 contributed greater decrease of signal gain comparing with PAMs of sgRNA1 and sgRNA3. These observations first proved that for the design of biosensing system to differentiate point mutation, recognizing a mutation inside the PAM region is a reliable strategy. Specifically, for our paired CRISPR array, mutations in the PAM regions of the overhang strand (5'-3') inhibit Cas9 recognition and cleavage activities toward the 5'-3' strand, therefore limiting the exposure of the overhanging region to the following DNA circuit. Without the exposed target information, the molecular cue to initiate of the PER cascade is lost, diminishing the overall signal gain.

To demonstrate the potential of this electrochemistry transduced integrated heterogeneous biochemical circuit on a realistic bioanalytical application, we challenged this integrated platform with human cell lysates spiked with the synthetic genome fragment of SARS-CoV-2. Owing to the modularity nature of the biochemical circuit (FIG. 4a), the reactants can be divided into two separate tubes and stored in 20° C. before usage. Also, the stability of the surface modified electrochemical sensor has also been verified suitable for long-term dry storage. These facts suggested that the combination of plug-and-play molecular components and a simple electrochemical system can be a potential platform for point-of-care diagnosis. Three different concentrations (50 nM, 25 nM and 10 nM) of synthetic COVID-19 genome fragment were prepared in human cell lysate. Comparable signals based on tests in human cell lysates with different gene concentrations were observed with previous buffer tests (FIG. 7D), confirming the potential of the developed platform for real sample analysis. Also, the interference studies based on a non-specific target (purple bars), the genome sequence of human papillomavirus 16, confirmed the specificity of this biochemical circuit.

The designed heterogeneous, multi-function biochemical circuit, by integrating with electrochemistry, provides a modular biosensing system for genetic analysis. The combination of CRISPR Cas9 D10A and the primer exchange reaction delivers a novel analytical strategy. Previous developed CRISPR based analytical platforms, which typically directly utilize CRISPR to detect and transduce the signal, limit the capability for downstream signal processing and the ability to utilize the target information to initiate new functions. In contrast, our system utilizes an array of paired Cas9 D10A, which can identify and transform inaccessible dsDNA in-formation into exposed ssDNA overhangs, providing diverse possibilities to connect and utilize the target sequence in-formation to initiate new functions. Moreover, by utilizing primer exchange reaction to further process the target, an autonomous synthesized ssDNA signaling strand can be produced in a programmable way, which demonstrates the generality of our biochemical circuit design. Through the combination of these two concepts with electrochemistry, a signal-on biosensing system able to perform genetic analysis with a high detection resolution is presented. One limitation of the biochemical circuit is the presence of reaction leakage, which is resulted from the spontaneous initiation of biochemical circuit without intended trigger. This phenomenon might be partially attributed to errors in chemical DNA synthesis. Further studies can also aim to evaluate the binding affinity of different protector strands toward the hairpin translator and the displacement kinetics of target gene on the protector strand. Defining an equilibrium state be-tween these two conditions can be beneficial to minimize the leakage reaction.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

We claim:

1. A CRISPR electrochemical biosensing system (E-CRISPR) for detection of analytes comprising:
   a disposable, micro-fabricated three-electrode sensor that includes a working electrode, a counter electrode, a reference electrode, and a nonspecific ssDNA reporter with an electrochemical tag for signal transduction tethered to a surface of the working electrode;
   a Cas12a-crRNA duplex that is designed to specifically recognize and cleave target nucleic acid strand based on a protospacer adjacent motif (PAM) sequence of the target nucleic acid strand and crRNA sequence, wherein the PAM recognition depends on specific 5' TTTN nucleic acid sequence located at an opposite strand of a recognition strand, and wherein only upon the recognition of the PAM sequence by the Cas12a protein, the Cas12a protein, acting as a DNA helicase, unwinds target DNA,
   wherein an electron transfer process between the working electrode and a redox active species on the nonspecific ssDNA reporter can be electrochemically initiated and transduced, with the presence of the target, Cas12a trans-cleavage activity is activated, cleaving the nonspecific ssDNA reporter off the working electrode surface, therefore decreasing the signal transduced, and
   wherein without the presence of the target, the Cas12a trans-cleavage activity is silenced, retaining the nonspecific ssDNA reporter on the working electrode surface.

2. The system of claim 1, further comprising an autonomous and programmable multi-functional heterogeneous biochemical circuit that can identify, transform, translate, and amplify detected biological or small molecule signals into physicochemical signals based on logic design principles, wherein biochemical circuit probes a specific biomolecular input, transforms the input into a structurally accessible form for circuit wiring, translates the input information into a prescribed arbitrary sequence, and finally amplifies the prescribed arbitrary sequence through autonomous formation of a signaling concatemer.

* * * * *